(12) United States Patent
Lee et al.

(10) Patent No.: US 9,950,097 B2
(45) Date of Patent: Apr. 24, 2018

(54) MULTIFUNCTIONAL CHITOSAN GRAFTED SURFACES AND USES THEREOF

(75) Inventors: Hyun-Su Lee, Wayne, PA (US); Russell Composto, Philadelphia, PA (US); David M. Eckmann, Wynnewood, PA (US); Noreen J. Hickok, Philadelphia, PA (US)

(73) Assignees: THE TRUSTEES OF THE UNIVERSITY OF PENNSYLVANIA, Philadelphia, PA (US); THOMAS JEFFERSON UNIVERSITY, Philadelphia, PA (US)

( * ) Notice: Subject to any disclaimer, the term of this patent is extended or adjusted under 35 U.S.C. 154(b) by 118 days.

(21) Appl. No.: 13/983,847

(22) PCT Filed: Feb. 7, 2012

(86) PCT No.: PCT/US2012/024141
§ 371 (c)(1),
(2), (4) Date: Nov. 20, 2013

(87) PCT Pub. No.: WO2012/109239
PCT Pub. Date: Aug. 16, 2012

(65) Prior Publication Data
US 2014/0114055 A1 Apr. 24, 2014

Related U.S. Application Data

(60) Provisional application No. 61/440,151, filed on Feb. 7, 2011.

(51) Int. Cl.
*A61L 29/08* (2006.01)
*A61L 31/10* (2006.01)
*B29C 47/00* (2006.01)
*B29C 49/00* (2006.01)
*B29C 51/00* (2006.01)

(52) U.S. Cl.
CPC .............. *A61L 29/085* (2013.01); *A61L 31/10* (2013.01); *B29C 47/0004* (2013.01); *B29C 47/0021* (2013.01); *B29C 49/0005* (2013.01); *B29C 51/002* (2013.01)

(58) Field of Classification Search
CPC ... A61L 29/085; A61L 31/10; B29C 47/0004; B29C 47/0021; B29C 49/0005; B29C 51/002
USPC .......................................................... 536/20
See application file for complete search history.

(56) References Cited

U.S. PATENT DOCUMENTS

| | | |
|---|---|---|
| 4,918,016 A | 4/1990 | Leuba et al. |
| 5,208,166 A | 5/1993 | Saunders et al. |
| 5,830,883 A | 11/1998 | Block et al. |
| 5,900,408 A | 5/1999 | Block et al. |
| 6,306,835 B1 * | 10/2001 | Daly et al. .................. 514/55 |
| 2003/0134120 A1 | 7/2003 | Kim et al. |
| 2003/0219533 A1 | 11/2003 | Chabrecek et al. |
| 2006/0134158 A1 | 6/2006 | Majima et al. |
| 2006/0177489 A1 | 8/2006 | Massouda et al. |
| 2007/0085059 A1 | 4/2007 | Mora-Gutierrez et al. |
| 2009/0032027 A1 * | 2/2009 | McCachren et al. .... 128/207.15 |
| 2009/0239084 A1 | 9/2009 | Bristow et al. |
| 2010/0003212 A1 | 1/2010 | Kis et al. |
| 2010/0291306 A1 | 11/2010 | Tsuchida et al. |

OTHER PUBLICATIONS

Lee et al., "The effect of non-specific interactions on cellular adhesion using model surfaces", Biomaterials 26, 2005, 1721-1730.

* cited by examiner

*Primary Examiner* — Yih-Horng Shiao
(74) *Attorney, Agent, or Firm* — Mark S. Cohen; Pearl Cohen Zedek Latzer Baratz LLP

(57) ABSTRACT

The invention relates to a multifunctional chitosan grafted surface. Specifically, the invention relates to a chitosan modified with a quaternary ammonium salt (CH-Q) grafted surface that provides various functional properties, including stability (pH 3-9) and unique pH dependent swelling and antibacterial properties.

20 Claims, 22 Drawing Sheets

US 9,950,097 B2

MULTIFUNCTIONAL CHITOSAN GRAFTED SURFACES AND USES THEREOF

CROSS-REFERENCE TO RELATED APPLICATIONS

This application is a National Phase Application of PCT International Application No. PCT/US12/24141, International Filing Date Feb. 7, 2012, claiming priority from U.S. Provisional Patent Application No. 61/440,151, filed on Feb. 7, 2011, both of which are hereby incorporated by reference in their entirety.

GOVERNMENT INTEREST

The work described herein was supported, in part, by a research grant (Grant No.: R01 HL060230) from the National Institute of Health, the United States Department of Heath and Human Services. The United States government may have certain rights in this application.

FIELD OF THE INVENTION

The invention relates to a multifunctional chitosan grafted surface. Specifically, the invention relates to a chitosan modified with a quaternary ammonium salt (CH-Q) grafted surface that provides various functional properties, including stability (pH 3-9) and unique pH dependent swelling and antibacterial properties.

BACKGROUND OF THE INVENTION

Chitosan, a cationic polysaccharide, is well-known as a biocompatible and biodegradable coating biomaterial. Due to its interesting features, chitosan has found use in medical and pharmaceutical applications such as drug delivery, wound dressing materials, and tissue materials. Recently, water-soluble chitosans have been synthesized to expand upon potential applications.

However, the application of chitosan is greatly limited, especially in biomedical materials, due to its inability to protect from harmful chemical and biological agents. While progress has been made in chitosan coatings on various surfaces, coatings still lack the ability to protect against changes in pH and microbial related damages.

Accordingly, there exists a need to develop multifunctional chitosan coated surfaces that provide protection against harmful chemical and biological agents.

SUMMARY OF THE INVENTION

In one embodiment, provided herein are chitosans modified with a quaternary ammonium salt.

In another embodiment, provided herein are articles, the articles comprising: a composition immobilized on a surface, wherein said composition comprises a chitosan modified with a quaternary ammonium salt.

In another embodiment, provided herein are methods, the methods comprising: producing a composition comprising a chitosan modified with a quaternary ammonium salt; and immobilizing said composition on a surface.

In another embodiment, provided herein are compositions, the compositions comprising: a chitosan modified with a quaternary ammonium salt, wherein said chitosan is operably linked to an antimicrobial molecule, an adhesion resistance molecule, a biocide leaching molecule, or a combination thereof, and wherein said composition is capable of being immobilized on a surface to provide an antimicrobial activity.

It is contemplated that whenever appropriate, any embodiment of the present invention can be combined with one or more other embodiments of the present invention, even though the embodiments are described under different aspects of the present invention.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

GFP-actin cells were seeded on PE films inserted on the bottom of 96 well plates. After 2 hr the culture medium was replaced with DHR-123 containing medium and cells were incubated for 2 hr at 37° C. Cells were rinsed twice with PBS, and $10^{-5}$ M of pargyline, a monoamine oxidase antagonist, or a superoxide initiator DMNQ was added to triplicate wells. Fluorescence (500 nm excitation, 536 nm emission) was measured at one hr. Higher values in the transduced cells are due to GFP expression. Results show identical trends in ROS production irrespective of GFP-actin treatment, thus strongly suggesting that the GFP-actin expression had no untoward effect upon normal MDM function. Data are presented as mean±SD (n=4 experiments). (C) Representative Western blot analysis of THP-1 GFP-actin expressing cell lysates immunoprecipitated with GFP-actin antibody and probed for the expression of the actin-binding protein Fascin.

Figure 11:
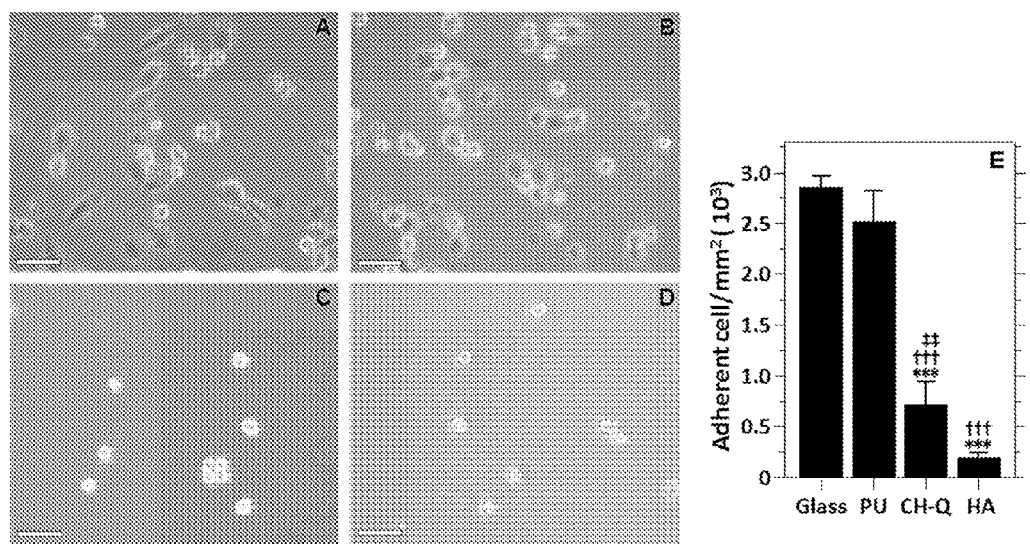

FIG. 11. Morphology of monocyte-derivatized macrophages (PMA-treated THP-1 cells) on (A) glass, (B) PU, (C) CH-Q, and (D) HA after three days. (A) Macrophages on the glass show amoeboid morphology, similar to macrophages adherent to polystyrene culture dishes. (B) Macrophages on PU demonstrate a round morphology. (C) Macrophages on CH-Q show a round morphology, a low cell surface density and small size, similar to cells attached to HA as shown in (D). Scale bar length is 50 µm. (E) Adhesion density of macrophages on the four surface types after three days. Data are presented as mean±standard deviation (n=3 experiments). Statistical significance: ***$P<0.001$ versus glass, †††$P<0.001$ versus PU, ‡‡$P<0.01$ versus HA, ‡‡‡$P<0.001$ versus HA.

Figure 12:
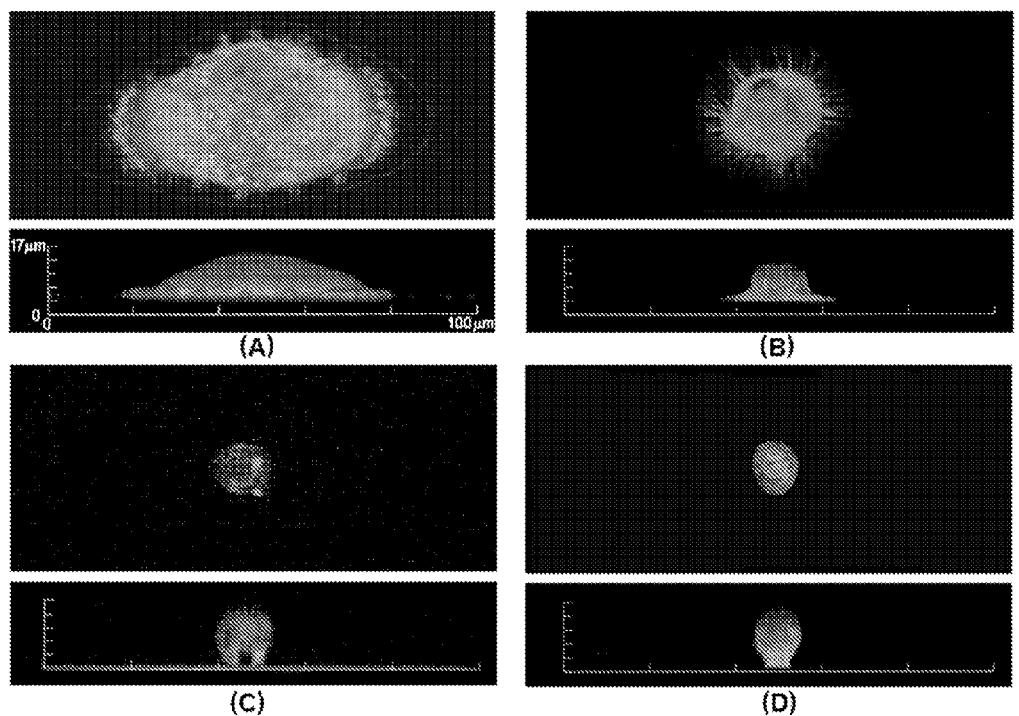

FIG. 12. Representative 3-D confocal fluorescence images of monocyte-derived macrophages (PMA-treated GFP-actin transduced THP-1 cells) on (A) glass, (B) PU, (C) CH-Q and (D) HA surfaces after three days of culturing. The images represent maximal cell projection along the optical axis (z-axis, top view in each panel A-D) and a side projection (y-axis, side view in each panel A-D). The identical y and z scales shown in (A) were used for all images.

Figure 13:
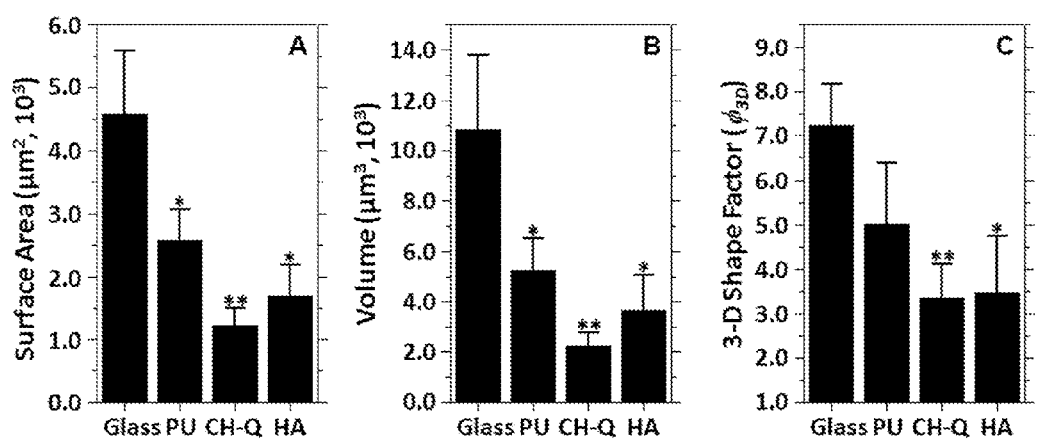

FIG. 13. (A) Cell surface area and (B) cell volume for macrophages adherent to glass, PU, CH-Q and HA surfaces. (C) Degree of cell spreading for macrophages adherent to the four surface types. The calculated 3-D shape factor $\varphi_{3D}=1$ for a perfectly spherical object. Data are presented as mean±standard deviation (n=3 experiments). Statistical significance: *$P<0.05$ versus glass, **$P<0.01$ versus glass.

Figure 14:
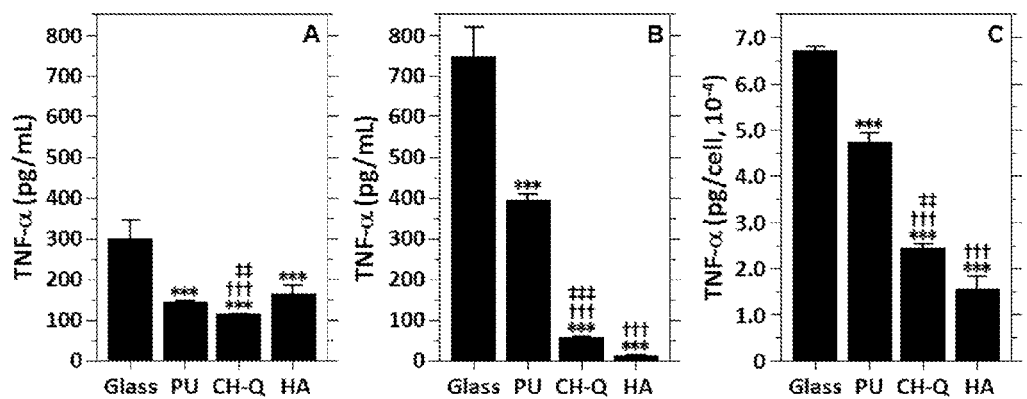

FIG. 14. (A) ELISA assay results of TNF-α levels secreted by suspended and adherent macrophages cultured in glass dishes and PU-coated, CH-Q coated, HA coated glass dishes for three days. (B) TNF-α secretion from adherent macrophages cultured for three additional days in each dish after rinsing and replacing the medium to remove suspended cells. (C) Normalized TNF-α secretion levels per adherent cell on each surface type. Data are presented as mean±standard deviation (n=3 experiments). Statistical significance: ***$P<0.001$ versus glass, †††$P<0.001$ versus PU, ‡‡$P<0.01$ versus HA, ‡‡‡$P<0.001$ versus HA.

Figure 15:
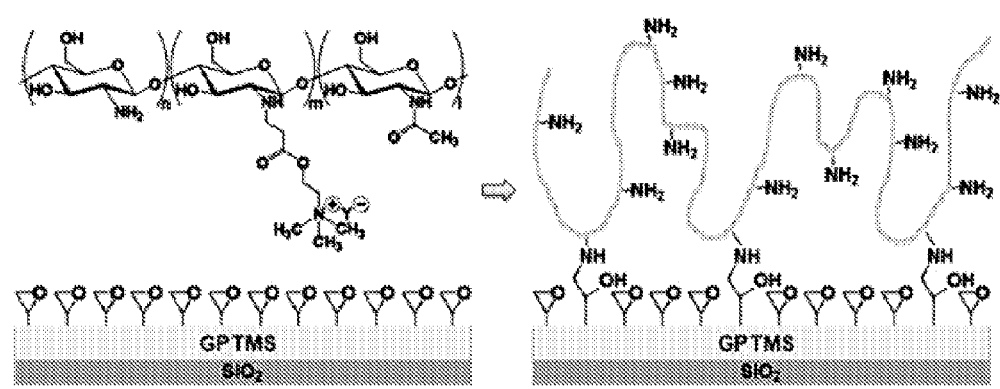

FIG. 15. The chemical structure of chitosan (CH, m=0, degree of deactylation: 87%) and chitosan modified with quaternary ammonium salts (CH-$Q_{25}$, m=0.27; CH-$Q_{50}$, m=0.51). Chitosans are "grafted to" epoxide-derivatized silicon oxide surfaces via the primary amine groups of chitosans. (left).

Figure 16:
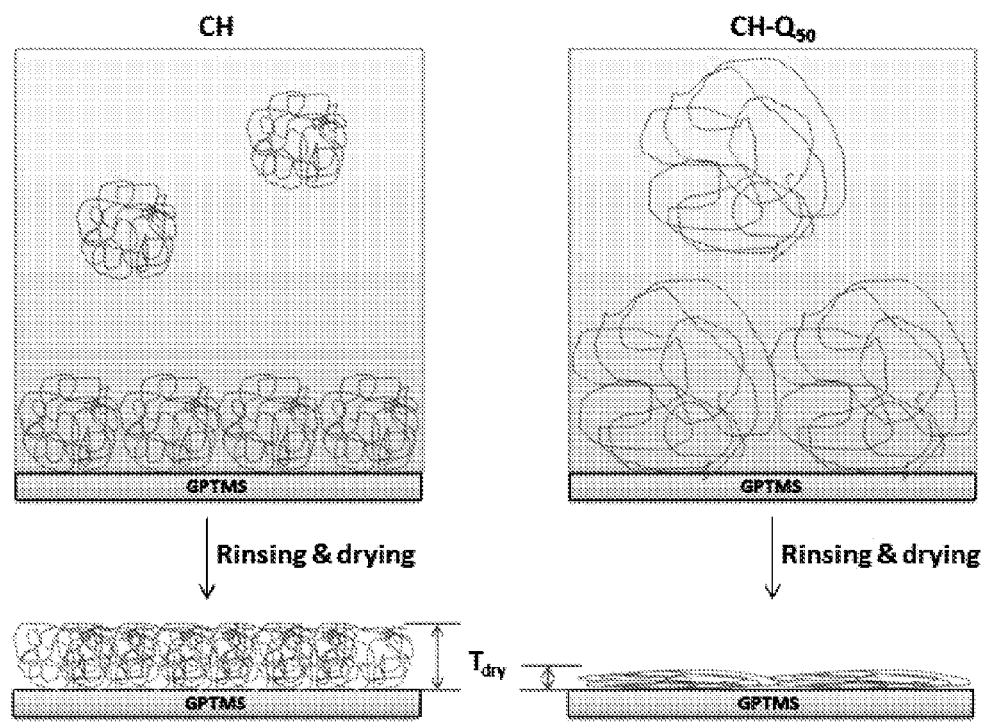

FIG. 16. The relationship between dry thickness and radius of gyrations, Rg, of CH, CH-$Q_{50}$, which are "grafted to" epoxide-derivatized silicon oxide surfaces in similar pH condition (~4.5).

Figure 17:
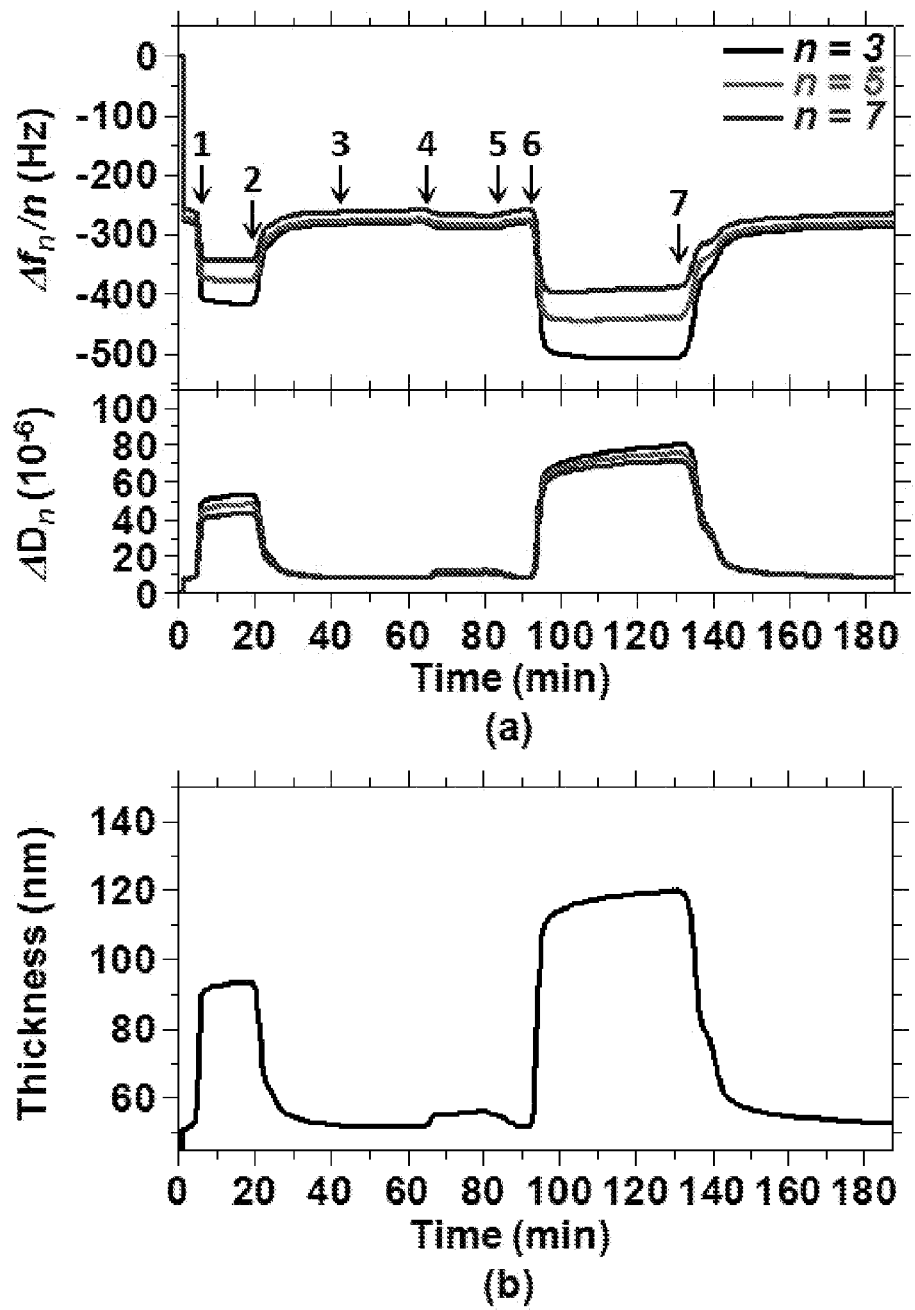

FIG. 17. (a) Traces of $\Delta f_n/n$ (n=3, 5, 7) and $\Delta D_n$ of CH layer versus time as a function of sequential changes on solution pH and counteranion types such as chloride and acetate counteranions. Arrows 1, 2, 3, 4, 5, 6, and 7 represent the change from pH 8.20 to pH 3.63 (with Cl⁻), pH 3.63 (with CP) to pH 8.20, pH 8.20 to 7.06, pH 7.06 to 5.46 (DI water), pH 5.46 (DI water) to 8.20, and pH 8.20 to 3.85 (with $CH_3CO_2^-$), and pH 3.85 (with $CH_3CO_2^-$) to pH 8.20. respectively. (b) Thickness versus time determined from the best fit for the experimental data with the viscoelastic model.

Figure 18:
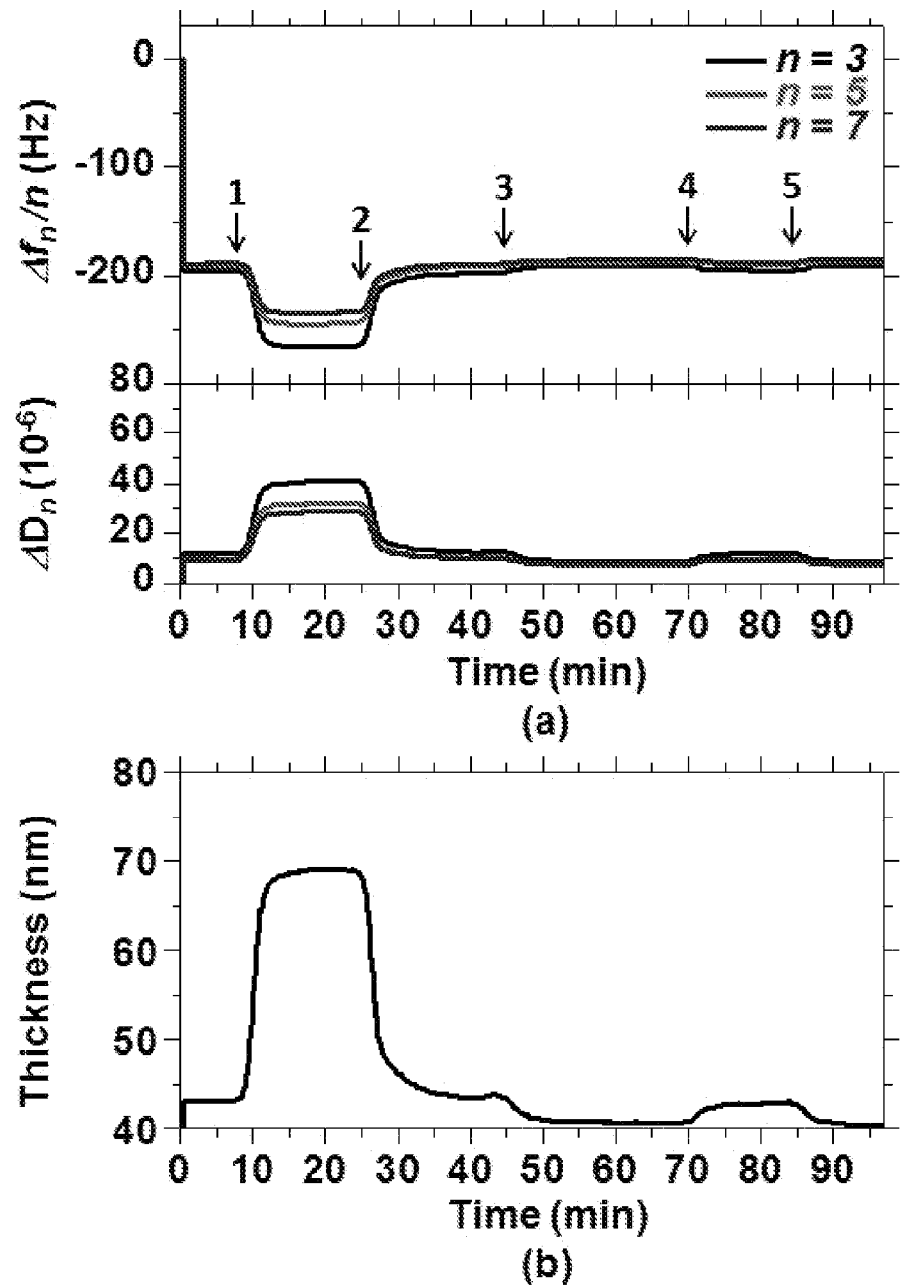

FIG. 18. (a) Traces of $\Delta f_n/n$ (n=3, 5, 7) and $\Delta D_n$ versus time for grafted CH-$Q_{25}$ as a function of sequential changes on solution pH. Arrows 1, 2, 3, 4, and 5 represent the change from pH 5.46 to pH 3.63 (with Cl⁻), pH 3.63 (with Cl⁻) to pH 5.46, pH 5.46 to 7.06, pH 7.06 to 5.46 (DI water), pH 5.46 (DI water) to 8.20, respectively. (b) Thickness versus time determined from the best fit from, the experimental data using the viscoelastic model.

Figure 19:
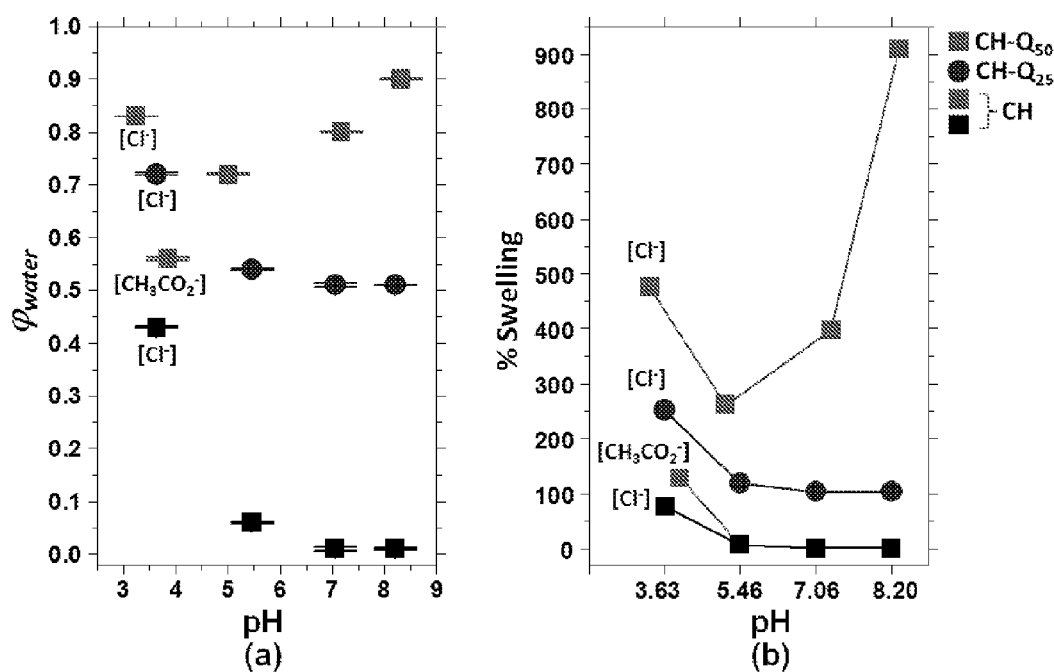

FIG. 19. (a) Infused water fractions in CH, CH-$Q_{25}$, and CH-$Q_{50}$ layers in each pH solution from in situ QCM-D. (b) Percent swelling of CH, CH-$Q_{25}$, and CH-$Q_{50}$ layers in each pH solution. [$CH_3CO_2^-$] represents pH 3.85 solution prepared with acetic acid. [Cl⁻] represents pH solution prepared with hydrogen chloride.

Figure 20:
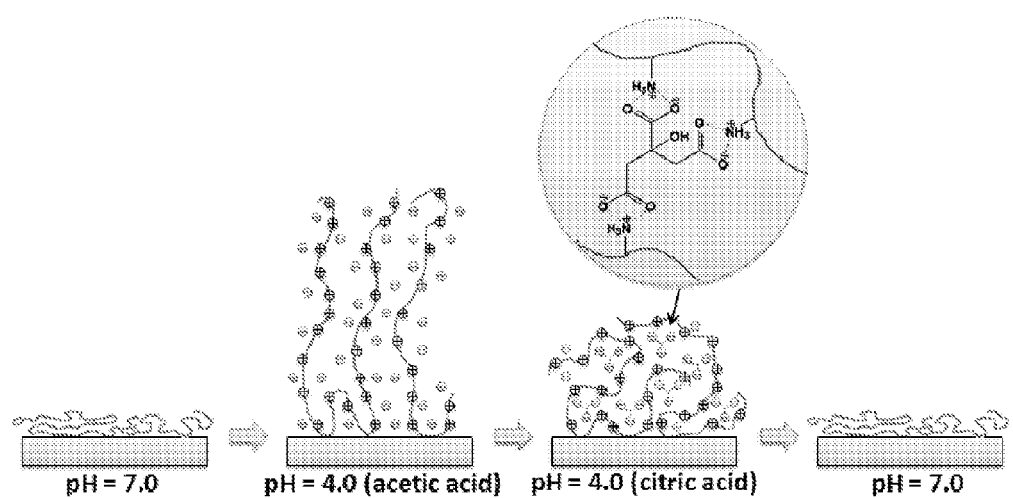

FIG. 20. Depicts changes in swelling of grafted CH-Q at different pH and counterion conditions.

Figure 21:
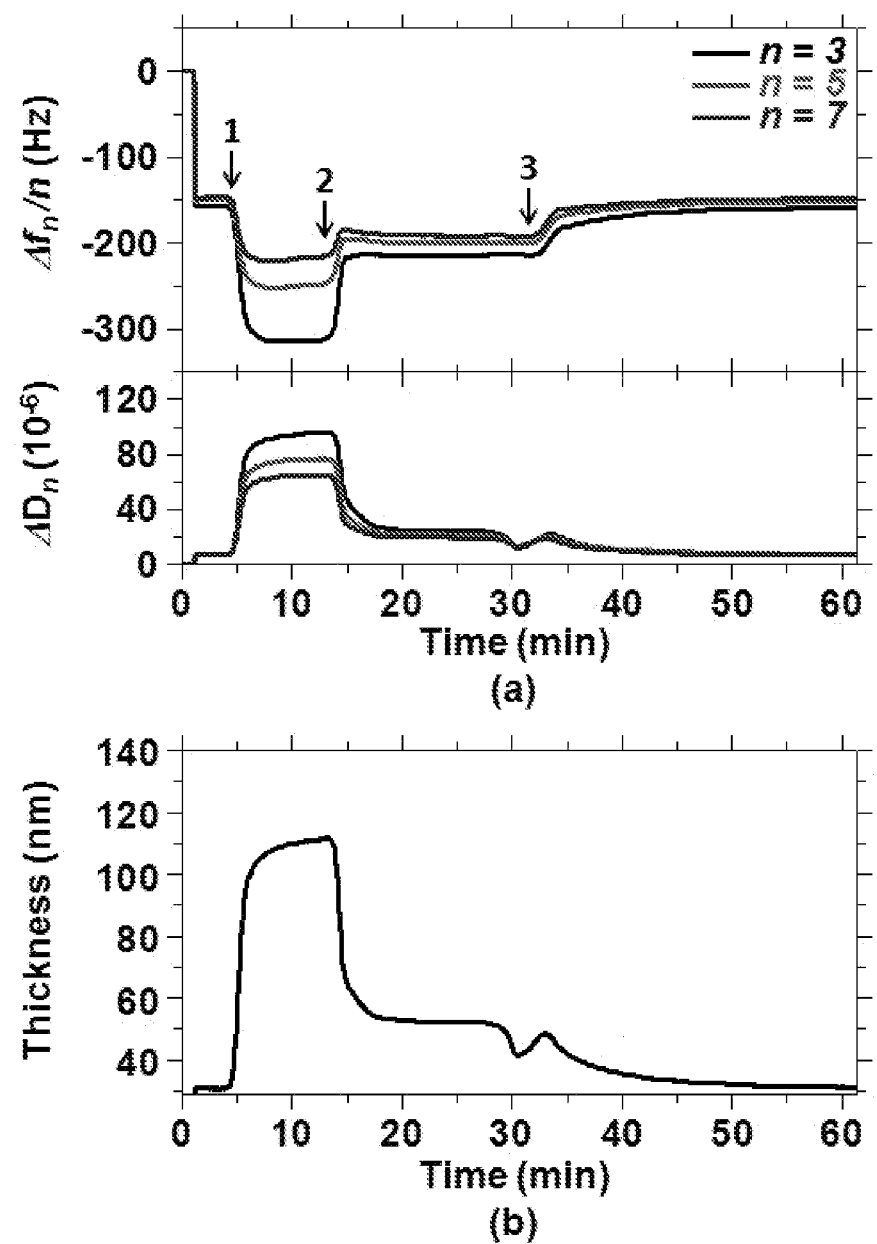

FIG. 21. (a) Traces of $\Delta f_n/n$ (n=3, 5, 7) and $\Delta D_n$ vs time as a function of sequential changes in solution pH. Arrows 1, 2, and 3 represent the change from pH 7.06 to pH 4.05 (with acetate anions), pH 4.05 to pH 4.08 (with citrate anions), pH 4.08 to pH 7.06, respectively. (b) Thickness versus time determined from the best fit of the experimental data with the viscoelastic model.

Figure 22:
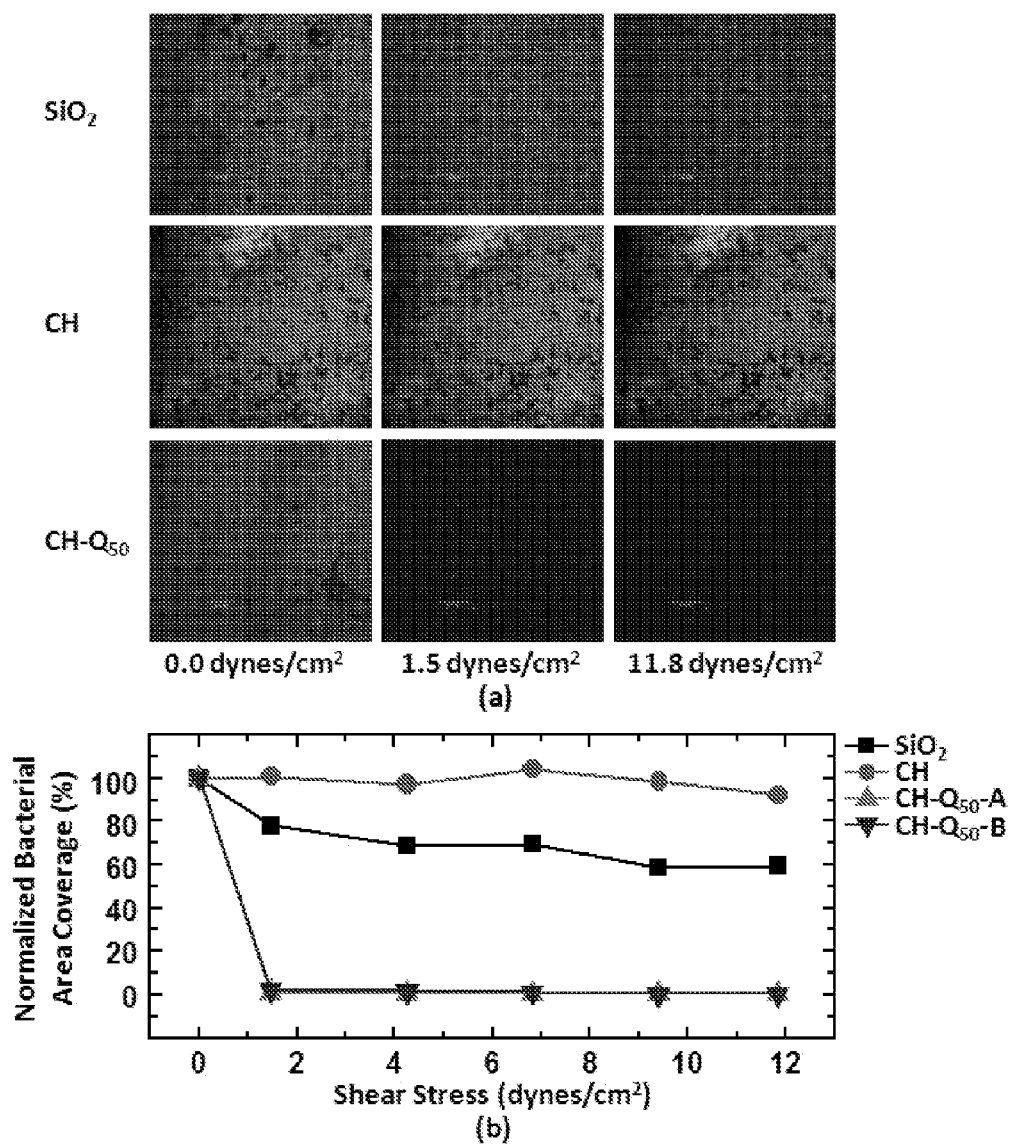

FIG. 22. (a) Confocal fluorescence images of bacteria on $SiO_2$, CH, and CH-$Q_{50}$ surfaces depending on different shear stresses (0, 1.5, and 11.8 dynes/cm²). (b) Normalized bacterial area coverage (%) depending on shear stresses (0, 1.5, 4.3, 6.8, 9.4, and 11.8 dynes/cm²)

DETAILED DESCRIPTION OF THE INVENTION

The invention relates to multifunctional chitosan grafted surfaces. Specifically, embodiments of the invention relate to chitosans modified with a quaternary ammonium salt (CH-Q) grafted surface that provides various functional properties, for example, stability (pH 3-9) and/or unique pH dependent swelling and/or antibacterial properties.

In one embodiment, herein are modified chitosans immobilized on a surface, wherein said chitosan is modified with a quaternary ammonium salt. In another embodiment, provided herein are articles, the articles comprising: a composition immobilized on a surface, wherein said composition comprises a chitosan modified with a quaternary ammonium salt. In another embodiment, provided herein are methods, the methods comprising: producing a composition comprising a chitosan modified with a quaternary ammonium salt; and immobilizing said composition on a surface.

In another embodiment, provided herein are compositions, the compositions comprising: a chitosan modified with a quaternary ammonium salt, wherein said chitosan is operably linked to an antimicrobial molecule, an adhesion resistance molecule, a molecule that prevents biocide leaching, or a combination thereof, and wherein said composition is capable of being immobilized on a surface to provide an antimicrobial activity.

The Applicants have surprisingly and unexpectedly found that a chitosan modified with a quaternary ammonium salt grafted on a surface provides various functional properties, including stability (pH 3-9) and unique pH dependent swelling and antibacterial properties. In one example, the Applicants surprisingly and unexpectedly found that a chitosan, modified with a quaternary ammonium salt, swells and shrinks in reversible manner depending on the changes in pH, and thereby provides stability of chitosan grafted surface in response to changing pH conditions. In another example, the Applicants surprisingly and unexpectedly found that a chitosan modified with a quaternary ammonium salt grafted on a surface exhibits antibacterial properties.

Chitosan is a polymer well known in the art and fully described in United States Patent Publications U.S. Pat. No. 5,900,408; U.S. Pat. No. 5,830,883; U.S. Pat. No. 5,208,166, U.S. Pat. No. 4,918,016; U.S. 20030134120; U.S. 20060134158; U.S. 20060177489; U.S. 20090239084; and U.S. 20100291306, all of which are incorporated by reference herein in their entirety.

Chitosan is a linear polysaccharide composed of randomly distributed $\beta$-(1-4)-linked D-glucosamine (deacetylated unit) and N-acetyl-D-glucosamine (acetylated unit). Chitosan can be produced by any method known to one of skilled in the art. In one embodiment, chitosan is produced by deacetylation of chitin, which is the structural element in the exoskeleton of crustaceans (e.g., crabs, shrimp) and cell walls of fungi. Chitin may be treated with strong alkalis to remove acetyl groups producing chitosan. Depending on the specific treatment of chitin, chitosan may vary in the degree of deacetylation.

In one embodiment, molecular weight of chitosan may range from about 1 to about 500 kDa. In another embodiment, molecular weight of chitosan may range from about 2.0 to about 250 kDa. In another embodiment, molecular weight of chitosan may range from about 3.0 kDa to about 75 kDa. In another embodiment, molecular weight of chitosan may range from about 3.5 kDa to about 50 kDa. In one embodiment, molecular weight of chitosan is 500, 300, 200, 150, 100, 50, 10, 5, 4, 3.5, 3, 2, or 1 kDa.

In some embodiments, chitosan may be in the form of a nanoparticle. As used herein, a "nanoparticle" is defined as a particle having a diameter of from approximately 1 to approximately 500 nanometer (nm), having any size, shape or morphology, known to one of skilled in the art. In one embodiment, the diameter of each nanoparticle ranges between 1 nm and 500 nm. In another embodiment, the diameter of each nanoparticle ranges between 50 nm and 300 nm. In another embodiment, the diameter of each nanoparticle ranges between 100 nm and 200 nm. In one embodiment, the diameter of each nanoparticle is about 500, 300, 200, 150, 100, 50, or 5 nm.

In particular embodiments, chitosan is modified with a quaternary ammonium salt. Quaternary ammonium salts are salts of quaternary ammonium cations with an anion. Quaternary ammonium cations, also known as quats, are positively charged polyatomic ions of the structure $NR_4^+$, R being an alkyl group or an aryl group.

Chitosan is modified with a quaternary ammonium salt by any method known to one of skilled in the art.

The modified chitosan may be operably linked to one or more other molecules, for examples, but are not limited to an antimicrobial molecule (e.g., antimicrobial peptide), an adhesion resistance molecule (e.g., polyethylene glycol), a biocide leaching molecule, or a combination thereof. In one embodiment, the term, "operably linked" may refer to chitosan and other molecules being arranged so that they function in concert for their intended purposes. In one example, the modified chitosan is operably linked to one or more other molecules by chemical conjugation. Other suitable methods known to one of skilled in the art may also be used.

The modified chitosan or a composition having the modified chitosan can be immobilized or otherwise grafted on any suitable surface. In one embodiment, the surface is a hard surface (e.g., metal, glass). In another embodiment, the surface is a soft surface (e.g., polymer). The immobilization or grafting methods may be chosen based on surface type or other factors, known to one of skilled in the art. For example, the well-known epoxide-amine reaction can be used to immobilize chitosan on various silicon oxide surfaces. Alternatively, chitosan can be further modified with 4-azidobenzoic acid to impart azide functional groups into the chitosan, and the azidated chitosan can be grafted onto amine-derivatized silicon oxide surface by, for example, photoreacting the amine and azidated CH-Q using UV.

Articles of the present invention have at least one layer of chitosan thereon. In some embodiments, articles of the present invention have a plurality of layers of chitosan.

The layer may be provided as a coating or as a preformed film which is secured to at least a portion of the implant and generally to an exterior surface thereof. The layer is preferably a self-adhering layer.

The layer secured to the implant may be of any desired thickness to serve the purpose. In one embodiment, the coating thickness ranges from about 5 nm to about 100 nm. In another embodiment, the coating thickness ranges from about 10 nm to about 80 nm. In another embodiment, the coating thickness ranges from about 30 nm to about 70 nm. In another embodiment, the coating thickness ranges from about 40 nm to about 60 nm. In one embodiment, the coating thickness is 100, 90, 80, 70, 60, 50, 40, 30, 20, 10, or 5 nm.

In some embodiments, the modified chitosan grafted on a surface results in improved stability of the chitosan coating. In some embodiments, the modified chitosan grafted on a surface results in improved antimicrobial (e.g., antibacterial) property of the chitosan coating.

Articles comprising the chitosan coated surface of the present invention may be in the form of or comprise a film, membrane, laminate, fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, spinning, spunbonding, melt blowing, spunlacing, or carding.

The articles of the present invention provide multiple uses, because many articles benefit from a reduction in microbial growth and a wide variety of polymers are included in the present invention.

Examples of applications include, but are not limited to, antibacterial, biosensor, nano-fluidic, and drug delivery applications.

Articles of the present invention can be used in wide variety of products, for example, but not limited to, medical materials, devices, or implants, such as bandages, adhesives, gauze strips, gauze pads, medical or surgical drapes, syringe holders, catheters, sutures, IV tubing, IV bags, stents, guide wires, prostheses, orthopedic pins, dental materials, pacemakers, heart valves, artificial hearts, knee and hip joint implants, bone cements, vascular grafts, urinary catheter ostomy ports, orthopedic fixtures, pacemaker leads, defibrillator leads, ear canal shunts, cosmetic implants, ENT (ear, nose, throat) implants, staples, implantable pumps, hernia patches, plates, screws, blood bags, external blood pumps, fluid administration systems, ventilators, endotracheal tubes, heart-lung machines, dialysis equipment, artificial skin, ventricular assist devices, hearing aids, and dental implants.

Medical equipment that comes into contact with the environment (e.g., ventilators, endotracheal tubes) can be coated with chitosan of the invention to provide antibacterial capability, such as MRSA resistance and for infection acquisition and transmission control. Chitosan can also be applied to implantable medical devices because it is biocompatible. Cell binding motifs can be attached to chitosan coatings so that tissue ingrowth can take place in conjunction with bacterial resistance.

The current invention is also useful in reducing or preventing biofilm growth on the surface of biomedical separation membranes, for example, but not limited to, pervaporation, dialysis, reverse osmosis, ultrafiltration, and microfiltration membranes.

Devices used in fluid, e.g., water, transportation and/or storage can also benefit from the antimicrobial material of the invention. Exemplary devices include, but are not limited to, pipes and tubes.

In order to impart antimicrobial functionality to the products listed herein, the product can be treated with the chitosan of the invention before it is manufactured, or after, or at any time during manufacture of the product. For example, in making an antimicrobial medical ventilator tube, material having a surface that comprises an effective amount of amino-reactive polymer can be treated according to the method of the invention, followed by fashioning a medical ventilator tube from the treated material. Alternatively, the chitosan treatment may be performed after the material is made into a medical ventilator tube.

The term "antibacterial," as used herein, may refer to bactericidal as is commonly known in the art. The number of bacteria present after contact with an antibacterial material is substantially reduced from the number initially present. The number of bacteria present is normally measured as colony forming units.

The term "antimicrobial," as used herein, may refer to antibacterial as well as having fungicidal and antiviral activities as is commonly known in the art.

The term "surface" may refer to the outer or topmost boundary of a material. Types of surfaces include properties such as being flat and solid such as of a film, fibrous as in fabric, porous as in a filter, rough, or permeable.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Figure 1:
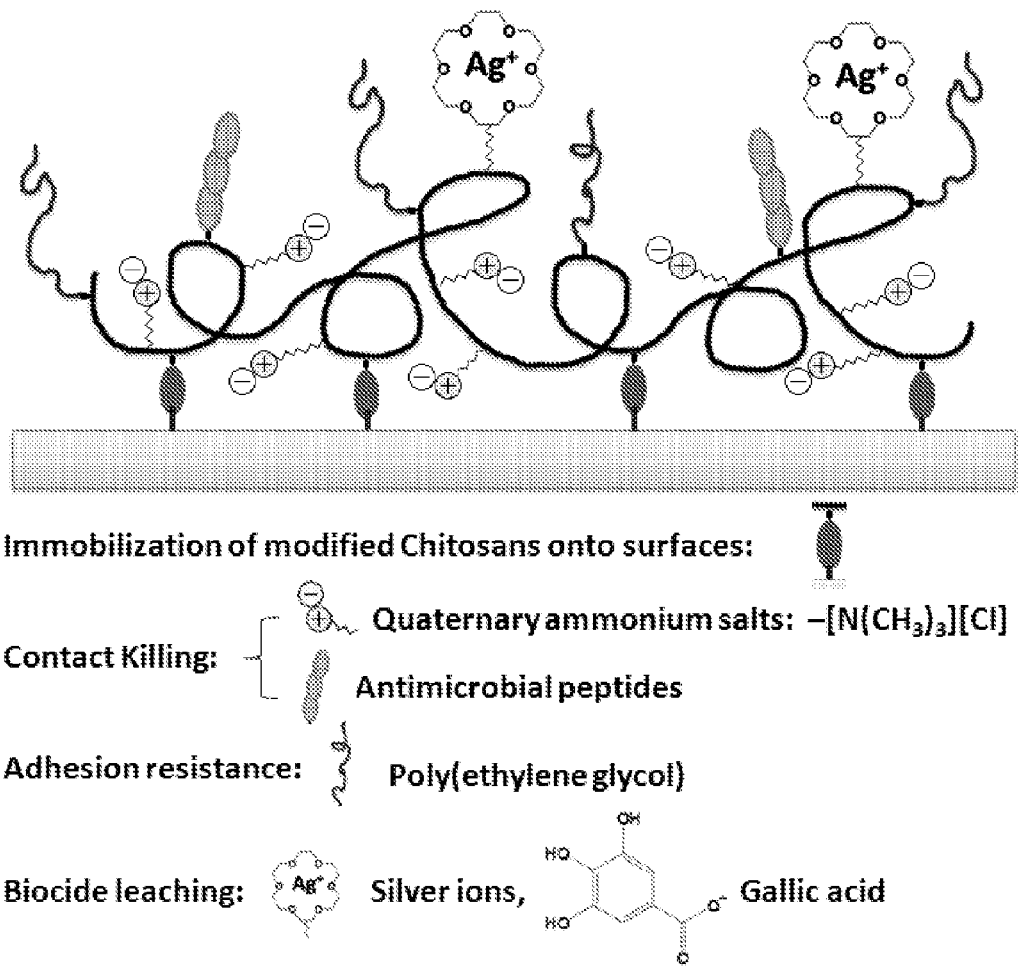
FIG. 1. Illustration of multifunctional surface composition with constituents incorporated to combat bacterial attachment and proliferation more effectively.

Example 1: Multifunctional Chitosan Grafted on Surfaces for Antibacterial, Biosensor, Nano-Fluidic, and Drug Delivery Applications Chitosan has been mainly studied as a bulk material and not as a surface coating. Chitosan does not exhibit adverse reactions in contact with cells and can be degraded by select enzymes; therefore, it is both biocompatible and biodegradable. Chitosan provides a structural backbone for multiple chemical attachments (quaternary ammonium salts, antimicrobial peptides, polyethylene glycol, silver ions, and others). Thus, as shown in FIG. 1, chitosan can be grafted to both hard (e.g., metal) and soft (e.g., polymer) surfaces by one of the previously described chemical methods. Chitosan can be designed to be multifunctional. For example, grafted chitosan can be modified with quaternary ammonium salts, polyethylene glycol and silver ions to impart contact killing, repulsion, and release characteristics into the coating.

Water-soluble chitosans with quaternary ammonium salts, CH-Q, were immobilized on silicon oxide surfaces using two complementary methods. The CH-Q layers were characterized by contact angle, zeta-potential, in-situ spectroscopic ellipsometry, SE, and in-situ quartz-crystal microbalance with dissipation, QCM-D. According to in-situ QCM-D and in-situ SE results, the CH-Q grafted layer was stable for pH values from 3 to 8, and exhibited fast, reversible swelling and contraction upon varying pH. A unique characteristic of the grafted CH-Q layer is that swelling was lowest near a pH of 5 but increased strongly (up to ~3x) above and below pH 5. Bactericidal efficiency using *S. aureus* showed that the grafted CH-Q layer exhibited excellent antibacterial activities compared to bare silicon oxide and APTES modified silicon oxide surfaces. The coverage of S, aureus colonies grown on APTES, $SiO_2$, and CH-Q surfaces was 219±74, 149±77, and 7±5 colonies/$cm^2$, respectively. The CH-Q grafted layers have many other potential applications because its backbone can be readily modified (FIG. 1).

Chemistry:

Water-soluble chitosans with quaternary ammonium salts, CH-Q, layers were immobilized on silicon oxide surfaces by two methods. In the first method, the well-known epoxide-amine reaction was used to immobilize CH-Q on various silicon oxide surfaces, including glass microscope slides, hydroxylated silicon wafers, and silicon oxide coated QCM sensors. Silicon oxide surfaces were modified with the silane, GPTMS, to create a surface with a high density of epoxide functional groups. CH-Q was grafted to this surface via the reaction of primary amines of CH-Q with the surface epoxide groups. In the second method, CH-Q was then modified with 4-azidobenzoic acid to impart azide functional groups into the CH-Q. This azidated CH-Q was grafted to amine-derivatized silicon oxide surface by photoreacting the amine and azidated CH-Q using UV. The azidated CH-Q allows for the photopatterning of surfaces as demonstrated in our study of azidated dextran (Coll-Ferrer, Langmuir 2010).

Because attachment takes place in water or upon exposure to UV radiation, the process to attach CH-Q to a surface does not expose the device to any potentially harmful chemicals: CH-Q attachment is an environmentally green process.

Figure 2:
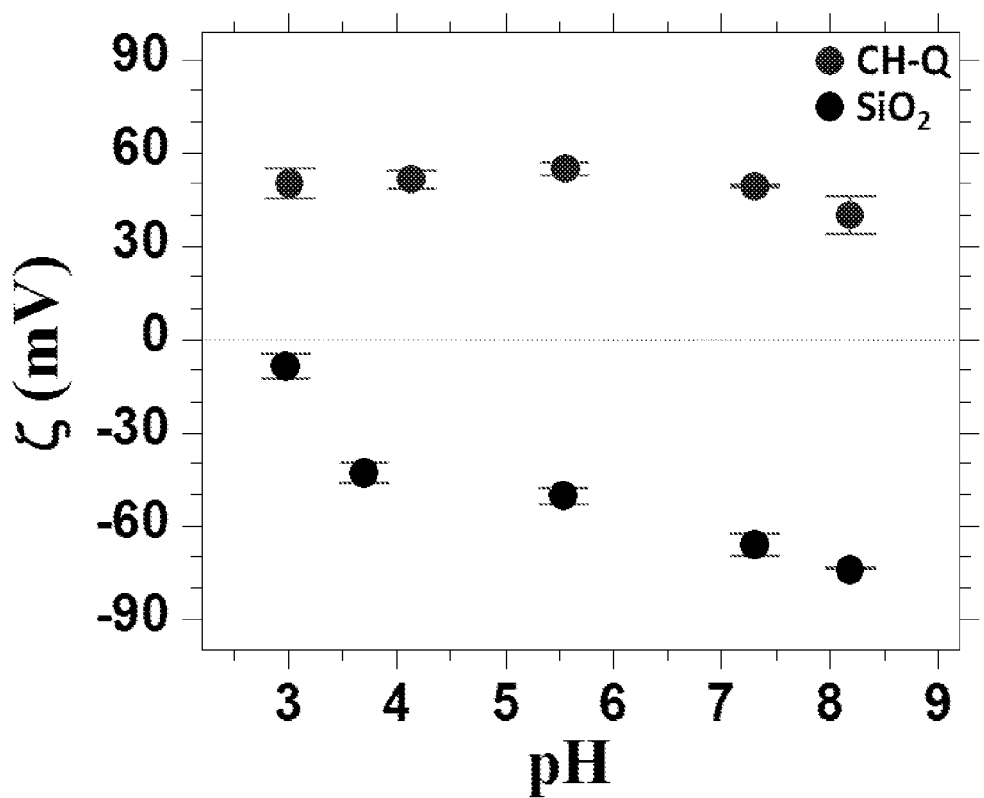
FIG. 2. Zeta potential of silicon oxide surface and grafted CH-Q for pH values from 2.97 to 8.21. The pH is varied by mixing HCl in $10^{-3}$ M TRIS and $10^{-3}$ M NaCl.

Characterization:

CH-Q and azidated CH-Q were characterized by FT-IR and $^1$H-NMR. The CH-Q grafted layers were characterized by contact angle, spectroscopic ellipsometry, and zeta-potential. The dry CH-Q grafted layer on GPTMS surfaces had a thickness of 6.0 nm and the dry UV-immobilized CH-Q layer on APTES surfaces had a thickness of 2.0 nm. Both layers were highly hydrophilic (water contact angles: ~0). Zeta potential measurements (FIG. 2) support the successful grafting of CH-Q because the surface charge changes from negative (silicon oxide) to positive (i.e., grafted CH-Q). This high positive zeta potential is maintained for pH values from 8 to 3. As shown in FIG. 2, the zeta potential of CH-Q immobilized surface at pH 8.19 is +39 mV. As pH is reduced to 7.30, the zeta potential increases to +49 mV and then remains relatively constant as pH is lowered further to 3.01. For biology applications, highly positive charged surfaces have been known to prevent nonspecific adhesion of similarly charged particles (proteins, bacteria, and cells) due to electrostatic repulsion.

Stable and Reversible Swelling:

According to in-situ QCM-D and in-situ SE measurements (FIGS. 3 and 4), immobilized CH-Q layer was chemically stable over a wide range of pH values and exhibited fast, fully reversible pH-dependent swelling & contraction (i.e., thickness changes), a characteristic that will allow immobilized CH-Q to be used as a biosensor and nano-fluidic controller. Another unique characteristic is that the swelling of the grafted CH-Q is not monotonic, swelling by a factor of two at pH values below and above 5.01.

Figure 5:
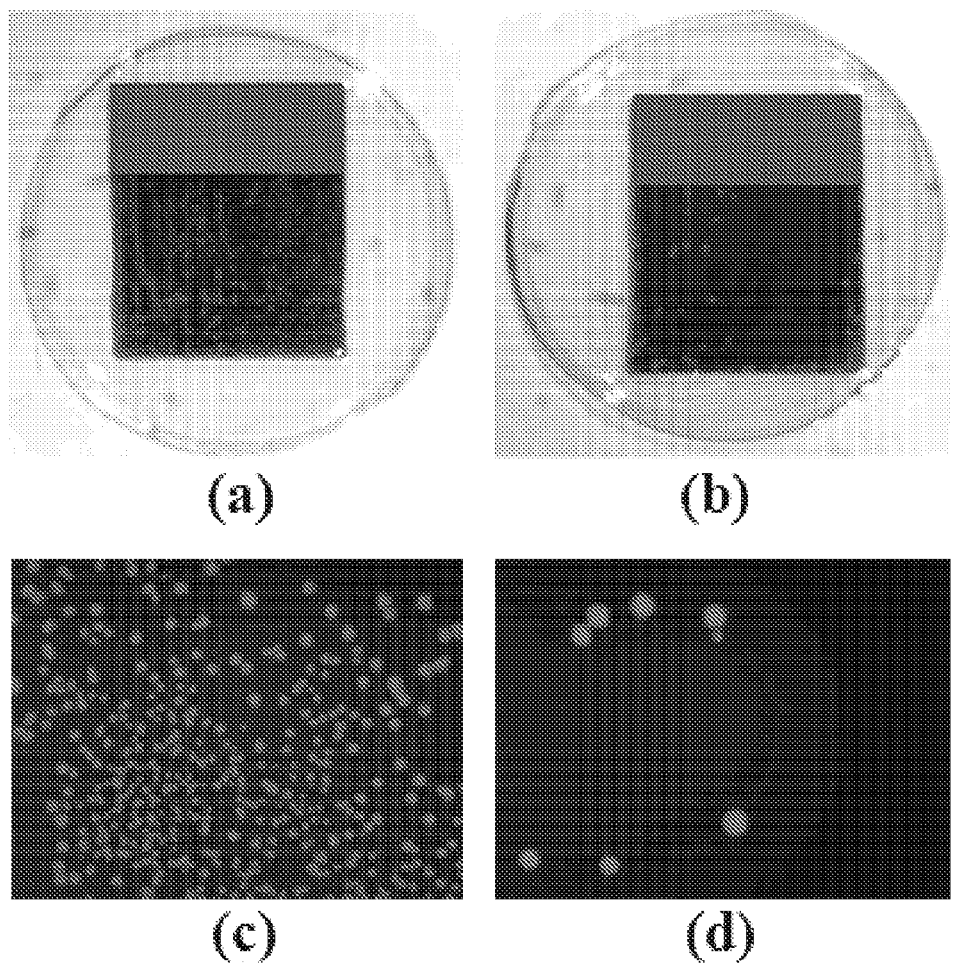
FIG. 5. (a) APTES surface and (b) CH-Q surface which were immersed in bacterial solution (S. aureus in BHI, ~$10^4$ cfu/mL) at 37° C. for 6 hrs with shaking at 100 rpm, immersed in sterilized PBS solution at 37° C. for 20 mins with shaking at 100 rpm, dried in air for 2 mins, and incubated under nutrition agar at 37° C. overnight. (c) photograph (1 cm×4/3 cm) of bacterial colonies on the APTES surface and (d) photograph (1 cm×4/3 cm) of bacterial colonies on the CH-Q surface.
Figure 6:
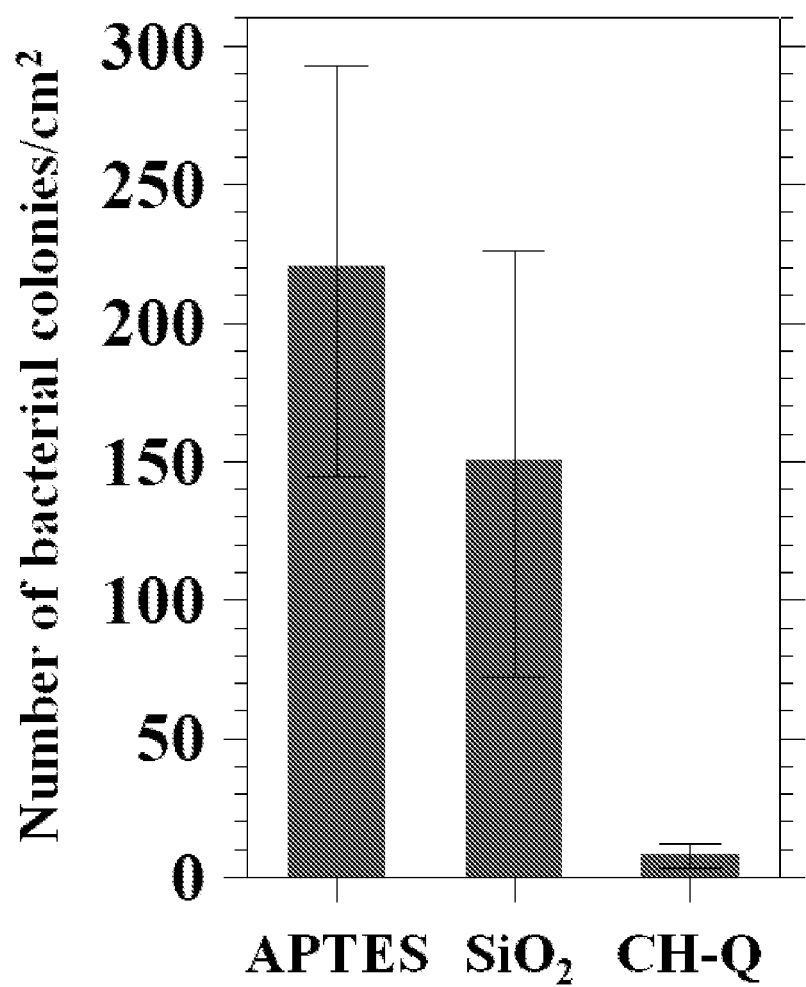
FIG. 6. Number of S. aureus colonies grown on APTES, $SiO_2$, and CH-Q surfaces. All experiments were performed at least three times and the colonies on all photographs (1 cm×4/3 cm) were counted. Average number and standard deviation error were used.

Antibacterial Properties:

According to bactericidal efficiency tests using *S. aureus* (ATCC 35556), a bacterium related to MRSA (Methicillin-resistant *Staphylococcus aureus*), the grafted CH-Q layer exhibited excellent antibacterial activity when compared with bare silicon oxide and APTES modified silicon oxide surfaces (FIGS. 5 and 6). The areal density of *S. aureus* colonies grown on APTES, $SiO_2$, and CH-Q surfaces was 219±74, 149±77, and 7±5 colonies/cm$^2$, respectively.

Bacterial adhesion can be measured directly on CH-Q modified surfaces. Drug delivery can be tested using QCM-D, IR and other methodologies. pH-dependent size selective nano-channels (i.e., nanofluidic valves) can be made for biology and other industrial applications. In order to make new multifunctional chitosan layers one can synthesize and use the chitosans with incorporation of several additional functional groups (e.g. antimicrobial peptides, polyethylene glycol, silver ions) as shown in FIG. 1.

Because of its reversible swelling behavior (i.e., thickness from 30 nm to 90 nm) pH-dependent, size selective nano-channels and pores can be prepared that can be size-tuned by varying the pH of the solution.

Besides its antibacterial behavior, the unique pH-dependent swelling behavior of CH-Q indicates that it could be utilized as a biosensor, antibacterial surface coating, drug releaser, and pH-dependent size-selective nanoscale.

Example 2: pH-Dependent Swelling of Grafted Chitosan on Surfaces

In this study water-soluble chitosan modified with a quaternary ammonium salt was prepared and immobilized on a surface, and the layer was characterized by means of in-situ quartz-crystal microbalance with dissipation, QCM-D, and in-situ spectroscopic ellipsometry, SE, measurements. The modified chitosan shows enhanced swelling at pH values below and above 5. The layer could be applied as biosensor, antibacterial, and drug delivery surfaces.

Experimental Details

Materials.

Chitosan Chiloclear® Cg-10 (Mw=60 kDa and degree of deacetylation: 87%) was received from Primex ehf., Iceland. Glycidoxypropyltrimethoxysilane (GPTMS, >98%), 80 wt % aqueous solution of [(2-(acryloyloxy)ethyl]trimethylammonium chloride (AETMAC), and anhydrous toluene (99.8%) were purchased from the Aldrich Chemical Co. USA. N-type, (100) oriented silicon wafers (CZ silicon: dopant, Ph: 20-30Ω resistivity) were purchased from Silicon Quest International, USA. QCM sensor crystals, An AT-cut piezoelectric quartz crystal (14 mm in diameter and 0.3 mm thickness) coated with a 50 nm-thick layer of silicon dioxide, were purchased from Biolin Scientific, inc. USA.

Polymer Synthesis.

Figure 7:
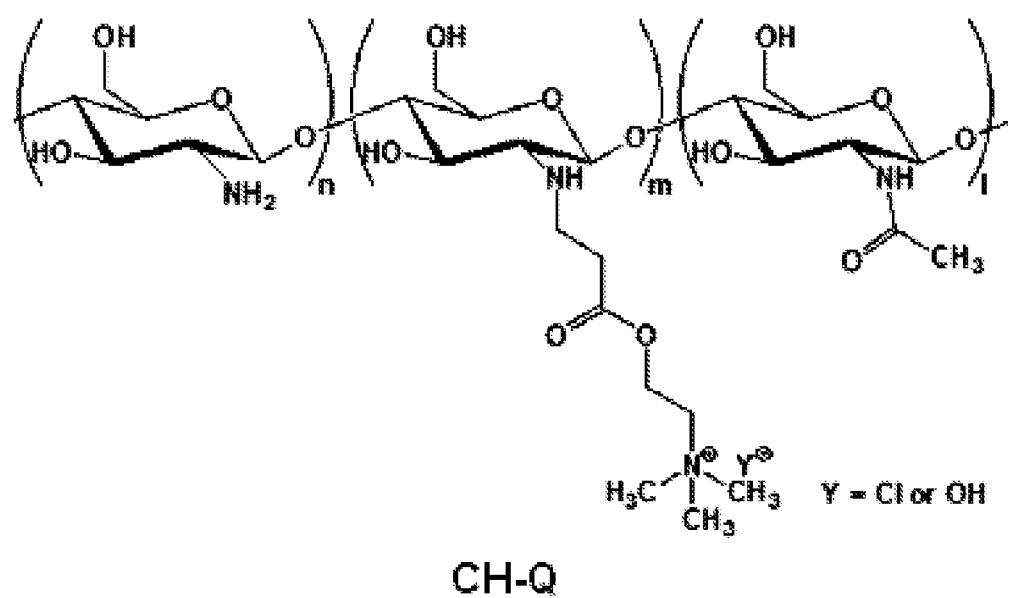
FIG. 7. The chemical structure of water-soluble chitosan with quaternary ammonium salts (CH-Q). The monomer fractions are n=0.13, m=0.51, and l=0.26.

Chitosan with quaternary ammonium salts, CH-Q (see FIG. 7) was prepared by Michael reaction of chitosan with acryl reagent (AETMAC) in water and characterized by using $^1$H NMR experiments according to the literature (Sashiwa, Biomacromolecules 2003). The degree of substation of the chotosan derivative, DS, was also calculated by using $^1$H NMR. For degree of deacetylation (87%, n=0.13), 51% of monomers are functionalized with quaternary ammonium salts (DS=m=0.51). Data for CH-Q (DS=0.51): $^1$H NMR (300 MHz, 0.5 M DCl in $D_2O$, ppm) 2.06 (s, 0.39H, $NHCOCH_3$), 2.91 (s, 1.01H, —$CH_2$—$CO_2$—), 3.13 (S, $NMe_3$), 3.28 (s, H-2 of GlcN), 3.31 (S, H-2 of N-alkylated GlcN), 3.6-4.1 (m, N—$CH_2$— and —$CH_2$—$CH_2$— of N-alkyl group, H-2 of GlcNAc, H-3,4,5,6 of GlcN and GlcNAc), 4.61 (br, H-1 of GlcNAc), 5.04 (br, H-1 of N-alkylated GlcN).

Surface Preparation and Characterization.

Silicon wafers (35 mm×15 mm) and $SiO_2$-coated QCM sensor crystals were cleaned by immersion in piranha solution, rinsed with ultrapure water (Millipore Direcl-Q, 18 MΩ cm resistivity), dried with $N_2$, and exposed to UV-Ozone to produce an homogeneous hydroxyiated surface and to remove impurities. The deposition of GPTMS on silicon oxide surface was performed by immersion of the wafers and crystals into a 2% (v/v) GPTMS solution in anhydrous toluene at 80° C. for 12 hours under $N_2$ condition. The deposited samples were sonicated in toluene to remove physically absorbed GPTMS and impurities on the surface. In order to prepare immobilized CH-Q layer the GPTMS deposited samples were immersed in 2 wt % aqueous solution of CH-Q for 12 hours. The CH-Q immobilized samples were rinsed with the ultrapure water to remove physically adsorbed CH-Q and impurities on the surface. For the surface characterization the thicknesses of dry substrate on the surface were measured by alpha-SE ellipsometer (J. A. Woollam Co. INC. NE, USA) equipped with wavelength range from 380 to 900 nm (70° angle of incidence). Contact angles were measured by using a 1 μL sessile drop method.

In-Situ QCM-D Measurements.

An E4 QCM instrument (Q-Sense Inc., Gothenburg, Sweden) was used to monitor the conformation changes of immobilized CH-Q layer on $SiO_2$-coated QCM sensor crystal depending on pH changes. Solution pH was measured with a dual pH/conductivity meter (Dever Instru. Co. USA). Solution pH was adjusted by titration with 1 M NaOH and 1 M HCl. All different pH solutions were degassed by using sonicator. The liquid medium was pumped by peristaltic pump at a rate of 20 μL/min through a flow cell with the sensor crystal. The temperature of the system was controlled to 21° C.

The QCM-D measurement is based on the resonance frequency change of a vibrating quartz crystal, a piezoelectric material, when mass is deposited on it. The deposited mass, Δm, has a relationship with the frequency change, Δf, according to the Sauerbrey equation, $$\Delta m = -C\Delta f_n/n$$

Where C is the mass sensitivity constant (C=17.7 ng cm$^{-2}$·Hz$^{-1}$ for an AT-cut, 5 MHz crystal) and n is the vibrational mode number (n=1, 3, 5, . . . ). In addition, the dissipation change, $\Delta D_n$, the loss of energy stored in a vibration cycle, indicates the physical characteristics of the deposited layer such as viscosity, elasticity, and so on. If $\Delta D_n$ is less than $2.0 \times 10^{-6}$ and the plots of $\Delta f_n/n$ under several modes are superimposed, the layer is elastic. On the contrary, if $\Delta D_n$ is more than $2.0 \times 10^{-6}$ and the plots of $\Delta f_n/n$ are not superimposed, the layer is viscoelastic.

In-Situ SE Measurements.

According to the literature (Itano, Macromolecules 2008), a homemade liquid cell was used to measure the swelling of the CH-Q layer on silicon wafer in different pH solutions. In-situ SE measurements were also carried out using Alpha-SE ellipsometer.

Results

For immobilization of CH-Q on silicon oxide surface, the well-known epoxide and amine reaction was used. According to $^1$H NMR results CH-Q has secondary and primary amine functional groups (n:m:l=0.13:0.51:0.26, in FIG. 7). The primary amine functional groups of D-glucosamine units react with the epoxide groups of GPTMS to make stable covalent bonds. Table 1 shows the thicknesses and contact angles of silicon oxide and GPTMS layer are reasonable values when compared with the literature (Lee, Biomaterial 2005). The CH-Q layer has a dry thickness of 6.0 nm and the water contact angle is ~0. This means that the CH-Q is chemically grafted to GPTMS and forms an immobilized layer with hydrophilic character.

TABLE 1

Ellipsometric thickness and contact angle of dry layers

| Layer | Thickness | Contact angle (°, Water) |
|---|---|---|
| SiO$_2$ | 1.6 | ~0 |
| GPTMS | 0.7 | 43. ± 2 |
| CH-Q | 6.0 | ~0 |

The swelling of the grafted CH-Q as a function of pH was investigated QCM-D. First we monitored $\Delta f_n/n$ (n=3, 5, 7), and $\Delta D_n$ for the bare SiO$_2$-coated QCM sensor because changes of the solutions can induce frequency and dissipation changes due to their different viscosities, elasticities, and so on. When pH solutions (pH 3.25, pH 5.01, pH 7.17, and pH 8.30) were successively introduced, $\Delta f_n/n$ was constant within ±0.5 Hz and $\Delta D_n$ was also consistent. This shows that upon switching between the different pH solutions the observed changes in frequency and dissipation for the grafted chitosan layer can be attributed to changes in the swelling (i.e. conformation) of the chitosan brush, not to changes of the solutions.

Figure 3:
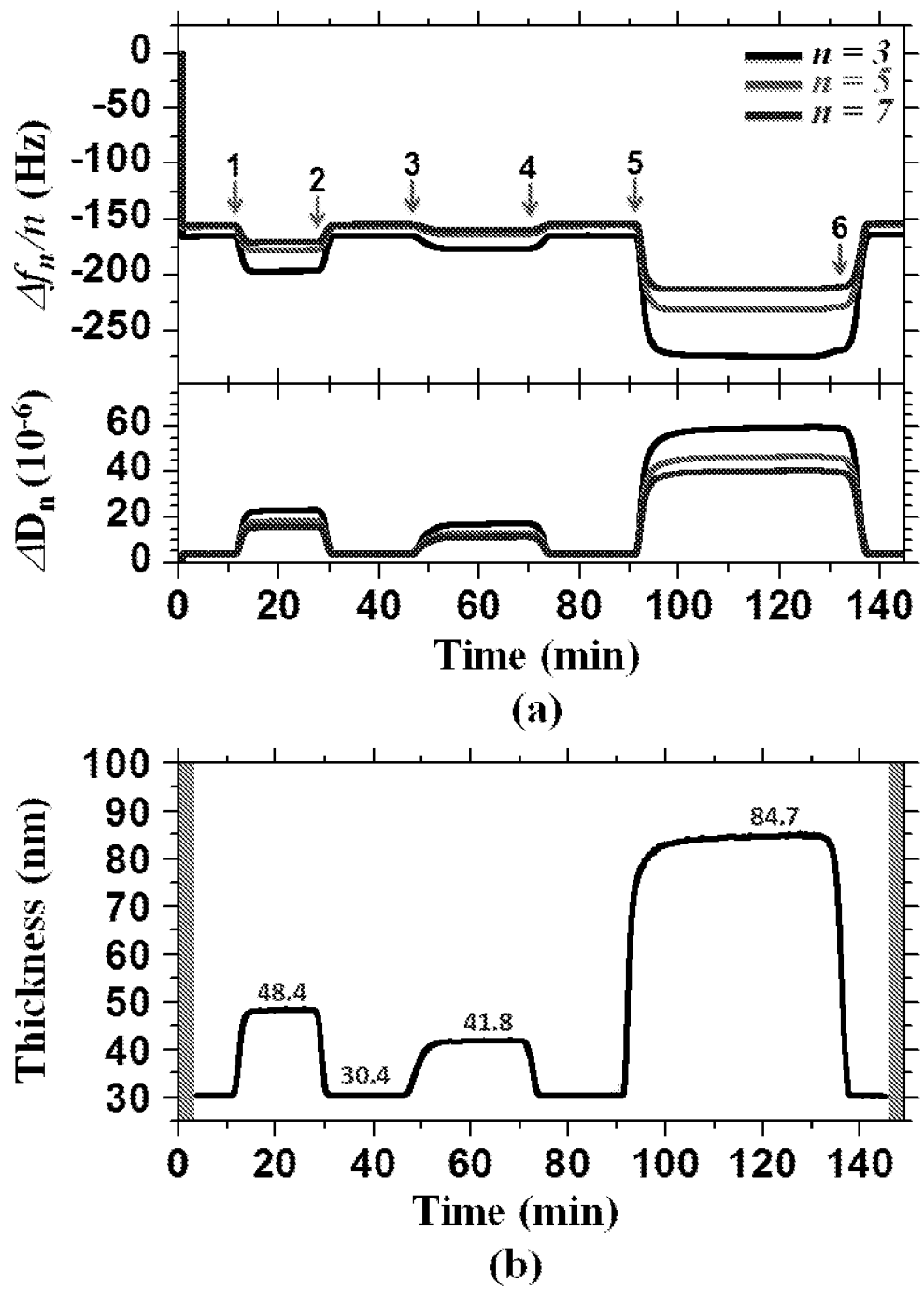
FIG. 3. (a) Traces of $\Delta f_n/n$ (n=3, 5, 7) and $\Delta D_n$ vs time as a function of sequential changes in solution pH. Arrows 1, 2, 3, 4, 5, and 6 represent the change from pH 5.01 to pH 3.25, pH 3.25 to 5.01, pH 5.01 to pH 7.17, pH 7.17 to 5.01, pH 5.01 to pH 8.30, and pH 8.30 to 5.01, respectively. (b) Thickness versus time determined from the best fit between the viscoelastic model and the experimental data shown in (a). The initial thickness, 30 nm, at pH 5.01 is recovered after every pH challenge to swell the CH-Q layer.
Figure 4:
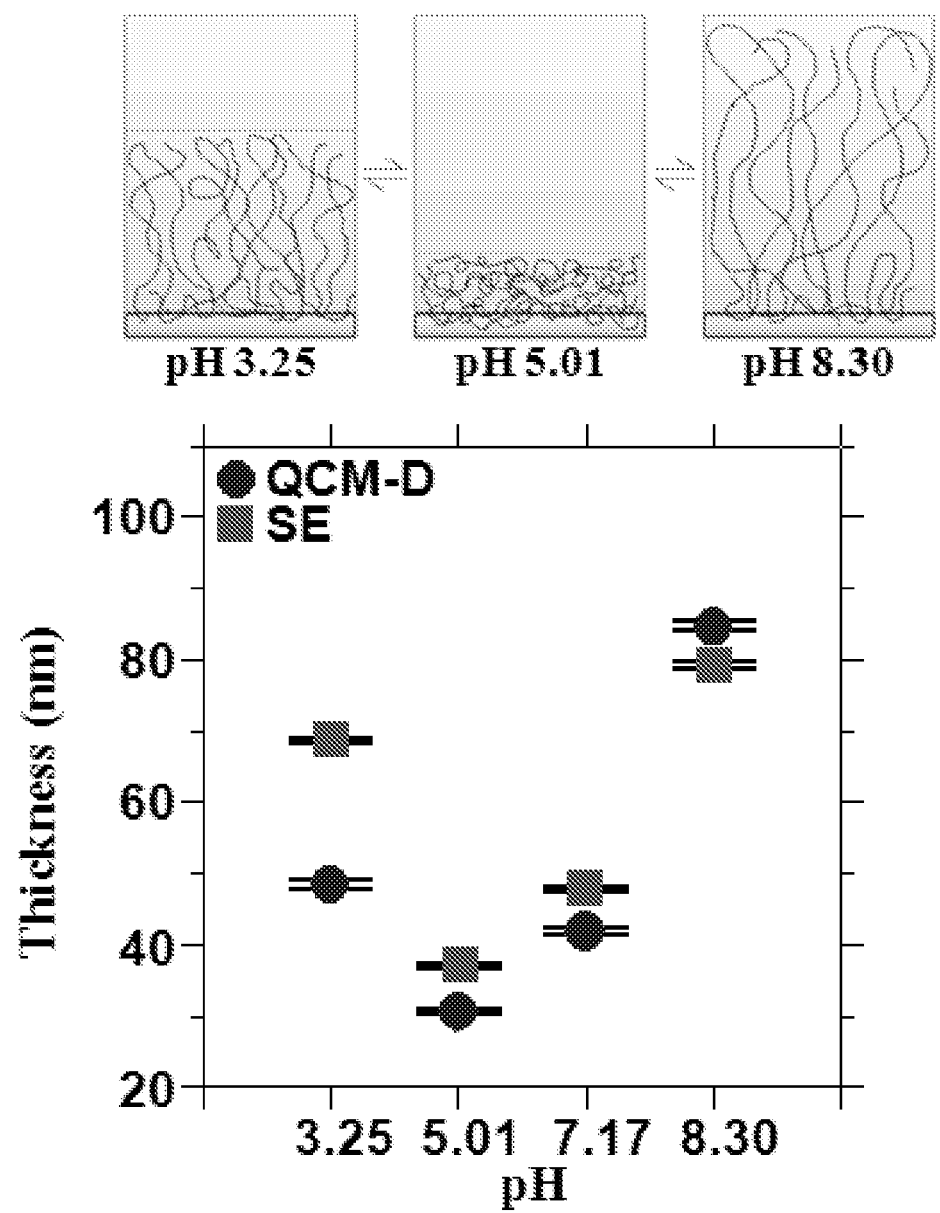
FIG. 4. Layer thickness as a function of solution pH, taken from in-situ QCM-D and in-situ SE experiments.

FIG. 3 (a) shows the QCM-D results for the immobilized CH-Q layer on the SiO$_2$ coated sensor upon switching the pH of the solution. Upon decreasing the pH from 5.01 to 3.25 (arrow 1), $\Delta f_n/n$ (n=3, 5, 7) decreased and no longer superimposed, and $\Delta D_n$ increased. This change suggests an increase in water content within the CH-Q layer at the lower pH condition resulting in a swollen and more viscous chitosan layer. Upon returning to pH 3.25 from pH 5.01 (arrow 2), $\Delta f_n/n$ (n=3, 5, 7) and $\Delta D_n$ returned to their original values. The increase of MA (n=3, 5, 7) and the decrease of $\Delta D_n$ mean that water is expelled from the layer resulting in a thinner more elastic chitosan film. Each change in pH (arrows 3, 4, 5, and 6) showed similar reversible behavior as before (arrow 1 and 2). Therefore, these studies demonstrate that immobilized CH-Q is chemically stable over a wide range of pH and swells and shrinks in reversible manner that depends on the changes in pH.

Table 2 shows that thicknesses measured by SE at each pH (i.e. static conditions), are similar to the thicknesses measured by QCM-D which is measured under flow at each pH.

TABLE 2

Thickness from in-situ QCM-D and in-situ SE data

| | Thickness (nm) | | | |
|---|---|---|---|---|
| Method | pH 3.25 | pK 5.01 | pH 7.17 | pH 8.30 |
| QCM-D | 48.4 + 0.69* | 30.4 ± 0.21* | 41.8 ± 0.45* | 84.7 ± 0.67* |
| SE | 68.6 + 0.39 | 36.9 + 0.32 | 47.8 ± 0.30 | 79.2 ± 0.47 |

*The thickness was obtained from the fitting program based on Voigt model.

Figure 8:
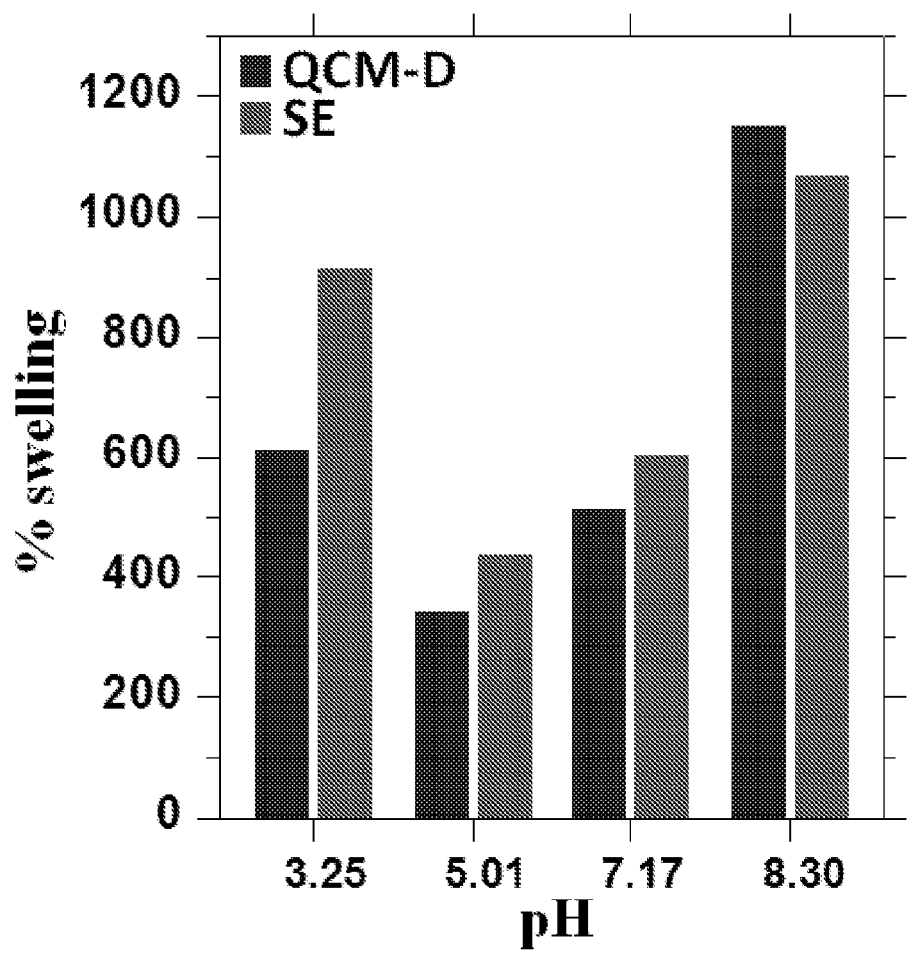
FIG. 8. The percent swelling of grafted CH-Q determined QCM-D and SE measurements at different pH conditions.

The thickness of the chitosan layer depends on pH. The percent swelling of the layer (table 2) was calculated relative to the dry layer thickness (6.72 nm). FIG. 8 shows the percent swelling of the CH-Q layers calculated from QCM-D and SE at different pH conditions. For pH 5.01, which represents the minimum thickness of the solution exposed layer, the CH-Q layer swells by 350% and 450% according to QCM-D and SE, respectively. One of most interesting observations is that CH-Q layer strongly swells (up to ~3×) upon raising or lowering the pH relative to 5.01.

Conclusion

Water-soluble chitosan with quaternary ammonium salts was immobilized on a GPTMS-coated silicon oxide surface. The swelling behavior of the layer as a function of pH was characterized by using both in-situ QCM-D and in-situ SE. Both measurements gave consistent results even though the measurements are made under flow and static conditions, respectively. The thicknesses of the layer depended on the solution pH because of an increase in water content at pH conditions above and below 5.

Example 3: Correlating Macrophage Morphology and Cytokine Production Resulting from Contact with Grafted Chitosan on Surfaces In this study, the morphological and inflammatory responses of adherent macrophages were correlated to evaluate the biocompatibility of surfaces. Monocyte derived macrophage, THP-1, and THP-1 cells expressing GFP-actin chimeric protein were seeded onto glass, polyurethane (PU), and glass surface modified with quaternary ammonium salt functionalized chitosan (CH-Q) and hyaluronic acid (HA). Using confocal microscopy, the surface area, volume and 3-D shape factor of adherent macrophages was quantified. For comparison, functional consequences of cell-surface interactions that activate macrophages and thereby elicit secretion of a pro-inflammatory cytokine were evaluated. Using an enzyme linked immune sorbent assay, tumor necrosis factor-alpha (TNF-α) was measured. On glass, macrophages exhibited mainly an amoeboid shape, exhibited the largest surface area, volume, and 3-D shape factor and produced the most TNF-α. On PU, macrophages displayed mainly a hemispherical shape, exhibited an intermediate volume, surface area and 3D shape factor, and produced moderate TNF-α. In contrast, on CH-Q and HA surfaces, macrophages were spherical, exhibited the smallest volume, surface area, and 3-D shape factor, and produced the least TNF-α. These studies indicate that macrophage morphology and cytokine secretion are correlated, suggesting that cell shape reflects the biocompatibility of surfaces.

The biocompatibility of synthetic and natural materials is of great interest, in part, because of the potential of new materials developed to replace body parts (e.g., tissue and organs) or function while in direct contact with living tissue. Despite advances in materials design, biomaterials do not behave like native biological structures and incite blood clotting and tissue inflammation, and are susceptible to infection. Thus, facile and accurate methods for screening and evaluating the biocompatibility of biomaterials are required. To avoid human risk and minimize animal experimentation with in vivo testing, in vitro methods such as cell and blood compatibility have been developed. Because of their characteristic response to foreign materials, macrophages are attractive cells for evaluating the biocompatibility of implants and medical devices.

Macrophages, derived from monocytes, play a key role in the phagocytosis of cellular debris and pathogens, as well as in the foreign body responses resulting from organ transplantation, biomaterial implantation, and microbe infection. Macrophages actively respond to many implants in vivo, including metals, ceramics, and polymers. In general, adherent macrophages on biomaterials react by attempting to phagocytose the foreign body. Subsequent pro-inflammatory cytokine secretion, such as release of tumor necrosis factor (TNF-α), interleukins (IL-1, IL-6), and chemokines (IL-8), directs the inflammatory and wound healing response to the biomaterial. Macrophages have been used to interrogate biomaterials by investigating their activity and secretion of pro-inflammatory cytokines.

The morphology of adherent macrophages on biomaterial surfaces and topographies has received limited attention. For example, adherent macrophages can exhibit an amoeboid, elongated spindle-like, or round shape depending on their lamellipodial extensions. Thus, spreading behavior is an indicator of cell morphological response to surface type and surface interactions. To quantify this response, cell attachment area has been measured using scanning electron microscopy (SEM), laser scanning confocal microscopy (LSCM), fluorescent microcopy, and bright field microscopy.

Although inflammatory cytokine-associated response to biomaterials is well known, the interrelationship between the morphological responses of macrophages with secretory function has received little attention. Here, we hypothesize that both macrophage morphology and secretory response reflect the biocompatibility of the surface and correlate with each other. Four complementary surfaces were investigated. Glass was used as a control surface. Polyurethane (PU) is a common biomaterial used in medical applications and is moderately biocompatible. A polymeric monolayer coating of chitosan modified with quaternary ammonium salts (CH-Q) was grafted to silicon oxide (glass). CH-Q is highly positively charged across a wide pH range, antibacterial and strongly swells at physiological conditions. To complement CH-Q, hyaluronic acid (HA), a negatively charged polymer, was grafted to silicon oxide (glass). Thus, macrophage morphology and secretory response can be compared on surfaces having widely different characteristics (e.g., charge). Cell morphology was used to interpret the response of adherent cells on each surface by measuring the cell-surface interfacial area, cell volume, and 3D shape factor. The secretion of the pro-inflammatory cytokine TNF-α, a classical in-vitro evaluation of biocompatibility, was monitored. These studies demonstrated that adherent macrophage morphology is integrally related to the cellular activation state resulting in cytokine secretion and that this response is decidedly surface type dependent. Whereas unmodified glass is known to stimulate significant biological responses, these studies show that PU provokes a greater biological response than glass surfaces functionalized with CH-Q or HA, which are the surfaces that elicit the minimum biological response.

Experimental Details

Materials.

Chitosan Chitoclear® Cg-10 (Mw=60 kDa and degree of deacetylation: 87%) was received from Primex ehf., Iceland. Polyurethane (Nalgene 280 PUR Tubing) and hyaluronic acid potassium salt from human umbilical cord (Mw=750 kDa, #H1504) were purchased from Fisher Scientific and Sigma-Aldrich Co., respectively. 80 wt % aqueous solution of [(2-(acryloyloxy)ethyl]trimethyl ammonium chloride (AETMAC), 3-Glycidoxypropyl-trimethoxysilane (GPTMS, ≥98%), 3-aminopropyltriethoxysilane (APTES, 98), tetrahydrofuran (for HPLC, ≥99.9%) and anhydrous toluene (99.8%) were purchased from the Aldrich Chemical Co. USA. Sodium cyanoborohydride ($NaBH_3CN$), and HEPES were purchased from Sigma-Aldrich Co. and Fisher Scientific. 1-Ethyl-3-(3-dimethylaminopropyl) carbodiimide hydrochloride (EDC) and sulfo-NHS were purchased from Thermo and Fisher Scientific, respectively. Ultrapure water (Millipore Direct-Q, 18 MΩ cm resistivity) was used for surface preparation.

Surface Preparation.

Glass Petri dishes and silicon wafers were cleaned using piranha solution (3:1 (v/v), $H_2SO_4$/30% $H_2O_2$) to create silanol groups that react with GPTMS and APTES, respectively. Using clean silicon oxide surfaces, GPTMS and APTES reactions were carried out immediately. The thickness and water contact angle of GPTMS and APTES grafted to surfaces were verified by ellipsometry (Rudolph AutoEL II) and contact angle goniometry, respectively. To graft, hyaluronic acid, HA, to surfaces, EDC-mediated condensation with N-hydroxysuccinimide was used. Specifically, the APTES (amine) glass surface was immersed in a solution containing hyaluronic acid (2 mg/mL), EDC (38.2 mg/mL), sulfo-NHS (10.8 mg/mL) and HEPES (2.3 mg/mL) for one day at room temperature. The HA grafted surface was washed with water and dried using nitrogen. Using a known method, chitosan with quaternary ammonium salts, CH-Q, was grafted to epoxide-derivatized (GPTMS) glass by immersing the GPTMS surface in 2 wt % aqueous solution (10 mL) of CH-Q (pH 7.8) at 60° C. for ~12 hr. The surface was rinsed with water to remove residual impurities. Polyurethane (PU) coated surfaces were prepared by spin coating (2000 rpm) a 3 wt % solution of PU in THF onto glass, followed by drying in vacuum for one day. The thickness and contact angle of HA, CH-Q and PU layers were determined by ellipsometer and contact angle goniometer for similar samples prepared on silicon.

Actin-GFP.

The plasmid pAcGFP1-Actin, encoding green fluorescent protein (GFP) and cytoplasmic β-actin, was purchased from Clontech (Mountain View, Calif.). Enzyme restriction digests were performed to insert the GFP-Actin fusion gene into a custom modified self-inactivating, replication incompetent HIV-1 based viral vector. The GFP-Actin fusion gene was inserted immediately downstream of the human CMV immediate early promoter. Viral vectors were generated in 293T cells and the supernatant was collected and processed as has been reported previously.

Macrophage Cell Culture.

The Human monocytes, (THP-1 obtained from ATCC and GFP-actin transduced THP-1), were cultured in RPMI medium (Cell Culture Technologies, VA), supplemented with 10% fetal bovine serum, 0.05 mM 2-mercaptoethanol, 200 mM L-Glutamine, and 1% Penicillin Streptomycin. As shown in FIG. 1, both monocytes were differentiated using 0.2 µM phorbol 12-myristate 13-acetate (PMA) and seeded on sample surfaces in the same cell culture condition, respectively. Both of these cell culture lines were maintained in a 37° C. incubator with 5% $CO_2$ and under a humidified atmosphere. Unless stated otherwise, experiments were conducted at a cellular concentration of $1.5 \times 10^5$ cell/mL.

Transduction of THP-1 Cells.

The human MDM cell line, THP-1, was grown in complete growth medium, supplemented with 8 µg/ml of polybrene, in the presence of the above described GFP-Actin expressing lentiviral vector (MOI=10) or a GFP expressing lentiviral vector. Fluorescence microscopy, using the appropriate filter set, was used to confirm the expression of both GFP and Actin-GFP. For experimental analysis, GFP expressing THP-1 cells (THP-1GFP) or GFP-Actin expressing THP-1 cells (THP-1$^{GFP-Actin}$), were transformed with the addition of 0.2 µM PMA to the media for one week prior to analysis as detailed below.

Western Blot Analysis and Immunoprecipitation Studies.

Cultured THP-1$^{GFP}$, or THP-1$^{GFP-Actin}$, cells were processed for Western blot analysis as previously described. Where indicated, an immunoprecipitation was performed as previously described. Briefly, cellular lysates were spun down at 10,000 g for 10 min, and the collected supernatant was first incubated with 5 µg of anti-GFP antibody (as above). The lysate proteins and immunoprecipitated proteins were resolved on a 4-15% gradient sodium dodecylsulfate-polyacrylamide electrophoresis gel using the method described by Laemmli Immunoblotting for the presence of GFP using a rabbit derived anti-GFP antibody (Abcam, Cambridge, Mass.) at the manufacturer's recommended dilutions in 10 mM pH 7.5 Tris-HCl, 100 mM NaCl, and 0.1% Tween 20 (TTBS) with 5% non-fat milk. In similar fashion, the immunoprecipitated Actin-GFP complex was processed to detect the presence of Fascin with a goat anti-human Fascin (Santa Cruz Biologics) antibody at the manufacturer's recommended dilutions. The respective immune complexes were detected with the species-appropriate, horseradish peroxidase-conjugated secondary antibodies in recommended dilutions in TTBS with 5% non-fat milk and were visualized with an enhanced chemiluminescence detection system on X-ray films.

DHR-123 Assay.

Reactive oxygen species (ROS) expression was determined as described previously using a dihyrdorhodamine-123 (DHR-123) detection assay as described previously. Briefly THP-1$^{GFP-Actin}$ cells or non-expressing THP-1 control cells were stimulated with PMA. After 1 week, attached differentiated THP-1 cells were trypsinized, seeded ($10^5$ cells/well), and allowed to spread onto the bottom of 96-well plates. Cells were incubated in serum-free media supplemented with 5 mM DHR-123 for two hr at 37° C. and then washed three times with PBS. Where shown, cells were incubated with $10^{-5}$ M Pargyline for two hours, and then 10 mM of DMNQ was added to the medium. After 2 hr, ROS levels were determined by monitoring the fluorescence of rhodamine generated by the oxidation of DHR-123. Fluorescence was measured at 500 nm (excitation) and 536 nm (emission) using a Spectramax Gemini series spectrofluorometer (Molecular Devices, Sunnyvale Calif.). Background fluorescence was subtracted from all readings and data were expressed as arbitrary fluorescent units (AFUs).

Cytokine Measurement.

Figure 9:
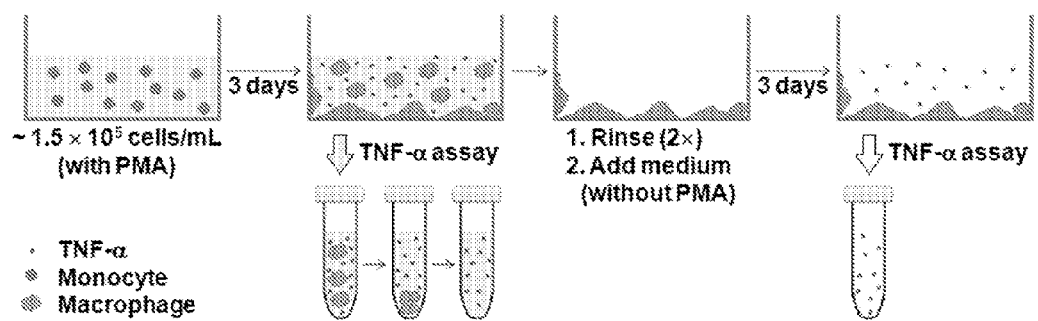
FIG. 9. Experimental scheme for measurement of TNF-α secretion by adherent macrophages (PMA-differentiated THP-1) on surfaces of glass, polyurethane (PU), chitosan possessing quaternary ammonium salts (CH-Q) and hyaluronic acid (HA). The cell culture medium volume is 7 mL for these experiments.

As depicted in FIG. 9, after three days in culture, TNF-α cytokines were measured for both non-adherent and adherent THP-1 cells, differentiated using 0.2 µM PMA. Fresh RPMI medium was used to rinse these plates and as well as only the adherent cells (c.f., FIG. 9). After an additional three days of culturing only adherent cells, the medium was collected to measure TNF-α using a commercially available (Invitrogen Corp. CA, USA) enzyme-linked immuno sorbent assay (ELISA) according to manufacturer's instructions. The TNF-α assay measurement was carried out at 450 nm optical density (OD).

Cell Morphology and Image Analysis.

As shown in FIG. 9, after three days in culture, non-adherent cells were removed using fresh RPMI medium. 2-D images of both macrophage lines and 3-D images of the GFP-actin macrophages were obtained using a Olympus FluoView FV1000 Confocal Microscope. To determine adherent cell volume, surface area, and the 3-D shape factor, sequential 2-D images were taken from the top to the bottom of adherent macrophages (slice width=0.5 µm). In order to compute total cell surface area and cell volume, values of the slice perimeter and area from each successive section were determined using ImageJ software from the National Institutes of Health. The cell volume and cell surface area, including the adherent cell-biomaterial surface interfacial area, were computed using a trapezoidal approximation between sections. The surface area and volume to calculate a 3-D shape factor, $\varphi_{3D}$, were also determined where:

$$\phi_{3D} = \frac{(\text{Surface Area})^3}{36\pi(\text{Volume})^2}$$

Statistical Analysis.

All data were expressed as mean±standard deviation. The Student's t-test (unpaired t-test) was used to evaluate data for significant differences between means. We accepted $P<0.05$ as an indication that statistically significant differences exist between the means.

Results

Transduction of THP-1 Cell with GFP-Actin and its Characterization.

Figure 10:
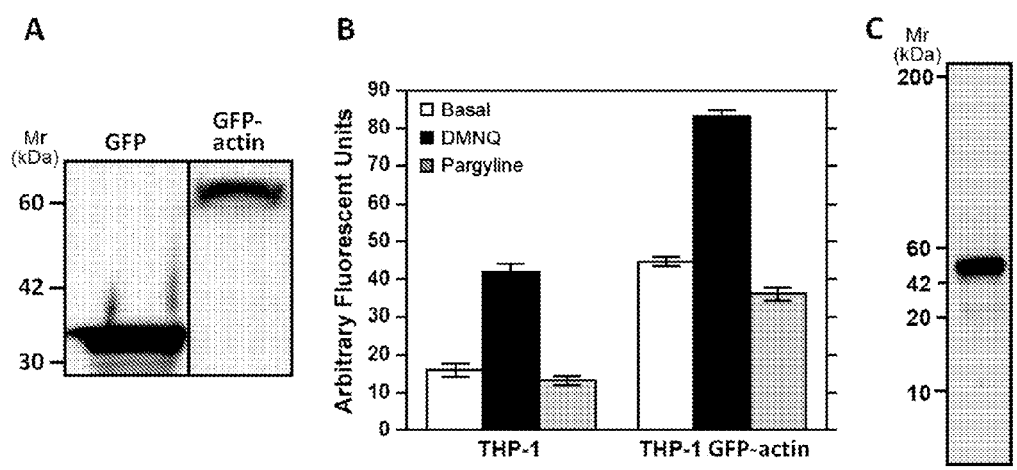
FIG. 10. (A) THP-1 was transduced with the GFP-actin gene via a lentiviral vector (THP-1 GFP-actin). Western blot analysis of GFP expression from THP-GA lysates expressing GFP control or GFP-actin confirms the presence of the chimeric protein. (B) Cultured THP-1 cells ($10^5$) or THP-1

We have successfully developed and characterized a lentiviral vector capable of transducing THP-1 cells with the chimeric protein GFP-actin gene. FIG. 10A is a representative Western blot analysis showing immunodetection of GFP from THP-1$^{GFP}$ or THP-1$^{GFP-actin}$ cell lysates. Lysates from THP-1$^{GFP}$ or THP-1$^{actin-GFP}$ show only a single immunoreactive band. As expected, the immune-detected band from resolved THP-1$^{GFP}$ lysates was ~30 kDa and is consistent with GFP expression. In contrast the band detected from THP-1$^{GFP-actin}$ was ~70 kDa, consistent with the presense of actin (40 kDa) and GFP (30 kDa). These results further confirmed expression of the GFP-actin protein. As the generation of ROS by monocyte derived macrophages has been shown by our group and others to contribute to the biodegradation of polyurethane elastomers, experiments were performed to ascertain if ROS production was affected by GFP-actin transfection. To that end, ROS levels were determined by monitoring the fluorescence of rhodamine generated by the oxidation of DHR-123. We compared the trends in ROS production between non-transfected and GFP-actin transfected THP-1 cells in the presence of known pharmacological agonists (DMNQ) or antagonists (Pargyline) to ROS production. As shown in FIG. 10B, identical trends in ROS expression are observed between the THP-1 and THP-1$^{GFP\text{-}actin}$ cells. Greater ROS expression was observed in the GFP-actin cells, as a result of GFP fluorescence Immunoprecipitation studies were conducted to identify actin binding proteins that associated with the chimeric GFP-actin protein. As shown in FIG. 10C, the actin binding protein Fascin was coprecipitated with the GFP-actin. These data strongly suggest that GFP-actin and native actin have similar characteristics.

Macrophage Adhesion and Morphology on Surfaces.

FIG. 11A-D shows representative 2-D images of adherent macrophages (PMA-treated THP-1 cells) on glass, PU, CH-Q and HA surfaces. On glass, macrophages adhered and spread significantly, showing an amoeboid morphology similar to the behavior on polystyrene culture dish (not shown). A minority of adherent macrophages also exhibited a round morphology. On polyurethane (PU) surfaces, the adherent macrophages, which spread moderately, exhibited a round morphology. On CH-Q, the adherent macrophages showed a round morphology, similar to the behavior on HA. The adherent macrophages on both CH-Q and HA also had much lower number density (fewer cells per field) and remained much smaller in their attached and spread shape in comparison to macrophages on glass and PU. In addition, the GFP-actin macrophages (PMA-treated GFP-actin transduced THP-1) on the different surfaces also exhibited a cell density, morphology and spreading behavior that was consistent with that observed for the non-GFP-actin transduced cells. FIG. 11E shows the surface density of adherent macrophages following surface rinsing described in FIG. 9. For glass and PU the cell densities were similarly high ($2.86\pm0.11\times10^3$ cell/mm$^2$, $2.52\pm0.30\times10^3$ cell/mm$^2$) By comparison, cell density was significantly lower on CH-Q ($7.1\pm2.2\times10^2$ cell/mm$^2$) and a full order of magnitude smaller on HA, on which were bound only $1.95\pm0.45\times10^2$ cell/mm$^2$.

3-D Morphology of GFP-Actin Transduced Macrophages on Surfaces.

After culturing the monocyte-derived macrophages (PMA-treated GFP-actin transduced THP-1 cells) on glass, PU, CH-Q and HA, the adherent cell morphology was analyzed qualitatively using 3-D images constructed from confocal fluorescence microscopy images. FIG. 12A-D shows the characteristic morphology of the adherent cells on each surface. The adherent macrophages on glass exhibited distinct lamelliopodial extensions and an amoeboid shape, as shown in FIG. 12A. The top panel in FIG. 12A also shows the actual extension of the cell boundary beyond the densely illuminated cell interior. This may result from the elongation of membrane-associated actin on the cytoplasmic surface of the membrane adjacent to the surface. Adherent macrophages on the PU surface are hemispherical as shown in FIG. 12B. The GFP-actin on the cytoplasmic surface of the attached cell membrane appears to radiate continuously from the cell, although the actual boundary of the adherent cell is not clearly demarcated. By contrast, the adherent cells on CH-Q and HA were both shown to exhibit a more spherical shape, as evident in FIGS. 12C and 12D. These images show that the cells have a lower interfacial contact area on CH-Q and HA, and lamelliopodial extensions are not well developed.

The values of the cell adhesion area, volume and shape factor on glass, PU, CH-Q and HA are given in FIG. 13. FIGS. 13A-B show that adherent macrophages on glass exhibited the largest total surface area ($4.6\pm1.0\times10^3$ µm$^2$) and cell volume ($10.8\pm2.9\times10^3$ µm$^3$). On PU, the total cell surface area ($2.6\pm0.5\times10^3$ µm$^2$) and cell volume ($5.5\pm1.3\times10^3$ µm$^3$) were significantly smaller than for glass, as were the surface area and volume on CH-Q ($1.2\pm0.2\times10^3$ µm$^2$ and $2.2\pm0.6\times10^3$ µm$^3$, respectively) and HA ($1.2\pm0.2\times10^3$ µm$^2$ and $3.6\pm1.4\times10^3$ µm$^3$, respectively). The computed values of 3-D shape factor appear in FIG. 5C. The value was found to be highest for glass ($\varphi_{3D}=7.2\pm0.9$), and by direct comparison significantly lower on both CH-Q ($\varphi_{3D}=3.3\pm0.7$) and HA ($\varphi_{3D}=3.5\pm1.2$). In comparison to glass, this parameter was not significantly different for cells on PU ($\varphi_{3D}=5.0\pm1.4$).

Macrophage TNF-α Secretion.

For the cell culture after three days that includes both suspended and adherent macrophages (FIG. 9), the concentrations of TNF-α secreted from both non-adherent cells and adherent cells on glass, PU, CH-Q, and HA surfaces, were $299.0\pm45.6$ pg/ml, $144.5\pm3.4$ pg/ml, $114.1\pm2.2$ pg/ml and $165.2\pm18.5$ pg/ml, respectively, as plotted in FIG. 14A. The levels of TNF-α secretion by cells exposed to PU, CH-Q, and HA surfaces were all statistically significantly lower than for those cells exposed to glass. TNF-α levels were also significantly lower for CH-Q than for either PU or HA.

At the three day time point for cell culture of solely adherent macrophages (suspended cells removed and fresh media having been instilled, see FIG. 9), the measured concentrations of TNF-α secreted by adherent cells on glass, PU, CH-Q, and HA surfaces were $746.6\pm71.5$ pg/ml, $394.9\pm15.1$ pg/ml, $58.0\pm1.6$ pg/ml and $12.7\pm2.8$ pg/ml, respectively, as provided in FIG. 14B. To provide a more specific index of cell activation by biomaterial surface contact to elicit secretion of pro-inflammatory cytokines, these TNF-α levels were normalized using the cell adhesion densities reported in FIG. 12E. Results appearing in FIG. 14C show that TNF-α secretion per adherent cell was highest on glass ($6.71\pm0.11\times10^4$ pg/cell). TNF-α secretion was significantly lower for cells adherent to PU ($4.74\pm0.18\times10^4$ pg/cell) and CH-Q ($2.46\pm0.07\times10^4$ pg/cell) surfaces. The lowest TNF-α levels were detected for cells attached to the HA surface ($1.57\pm0.26\times10^4$ pg/cell), and this was statistically significantly less than for any of the other surfaces tested.

Discussion

The primary focus of this research was to study the morphological response of macrophages attached to biomaterials and to determine the interrelationship between morphology and inflammatory cytokine-associated production to evaluate biocompatibility. We investigated the morphological response of adherent macrophages towards a hard inorganic material (i.e., glass), a relatively inert (i.e., polyurethane), and two glass surfaces coated with positively and negatively charged polymer brushes (i.e., CH-Q and HA). In parallel we also studied the functional consequences of adherent cell interactions with these surfaces to activate macrophages and thereby elicit secretion of the pro-inflammatory cytokines, TNF-α.

First, we successfully developed and characterized a lentiviral vector capable of transducing THP-1 cells with the chimeric protein GFP-actin gene. Identical trends in ROS expression observed between the THP-1 and GFP-actin transduced THP-1 cells and the co-precipitation of the actin binding protein Fascin with the GFP-actin demonstrated that the GFP-actin expression has no untoward effect upon normal monocyte derived macrophage function and GFP-actin has similar characteristics as native actin. In this study, PMA-stimulated THP-1 cells and GFP-actin transduced THP-1 cells, similar to the phenotype of human monocyte-derived macrophages, were employed. 2-D optical microscopy images and 3-D confocal fluorescence microscopy imaging reconstructions were used to assess cell density, volume, surface area, and spreading.

The morphological responses of monocyte-differentiated macrophages (PMA-stimulated THP-1) showed surface-dependent cell morphologies and population densities. Adherent macrophages on glass demonstrated primarily amoeboid and partially round morphologies, as has been reported. In contrast, adherent macrophages spread moderately and showed mainly a rounded shape on PU, a common biomaterial with moderate biocompatibility.[30,33,34] The cell population density was considerably higher on both glass and PU than was found on HA and CH-Q (FIG. 11E). Adherent macrophages on HA, a hydrophilic anionic polymer, did not spread and showed a round morphology. Moreover, macrophages attached to HA had the lowest number density of cells. Although the cells attached to CH-Q, a hydrophilic cationic polymer, exhibited a morphology similar to HA, the surface density was larger. Recently, we showed that adherent macrophages on CD47-functionalized surfaces exhibited a rounded morphology and had a surface density similar to the CH-Q and HA-functionalized surfaces. Our results for macrophage adhesion on these surfaces agree with findings reported by Brodbeck et al., who demonstrated that rank order of hydrophilic, anionic, cationic and hydrophobic biomaterial surfaces were associated with increasing quantities of macrophage adhesion. Although the specific molecular mechanism by which macrophages attach onto a surface has not been fully revealed, a lower density of macrophages indicates better biocompatibility of the surface.

To provide further details, confocal fluorescence microscopy was used to produce 3-D images of macrophages attached to the surfaces. The resultant data include cell surface area and volume, and a 3-D shape factor ($\varphi_{3D}$) which reflects cell spreading (FIG. 13). First, 3-D imaging of adherent macrophages on glass showed a preference for elongation of membrane-associated GFP-actin as well as distinct lamelliopodial extension, with resultant amoeboid morphology. This morphology has been observed by others. Of particular interest is that GFP-actin on the cytoplasmic surface of the attached cell membrane on PU surfaces stretches radially outward from the cell center, in contrast to cell behavior on glass. GFP-actin did not exhibit a similar behavior for cells attached to either CH-Q or HA. Recently, we showed that the polymerized state of actin (i.e., actin elongation) in adherent macrophages correlated with the biocompatibility of surfaces. Specifically, macrophages showed a significantly reduced affinity for polymeric surfaces modified with recombinant CD47, a ubiquitously expressed transmembrane protein that reduces the polymerized state of actin through signaling mechanisms mediated by its cognate receptor, Signal Regulatory Protein alpha, or SIRPα. We surmise that actin extension is one potential method to evaluate surface biocompatibility. Second, 3-D quantitative analysis of cell morphology indicates that macrophage surface area and volume as well as spreading behavior depend on surface type. In this regard, the morphology of adherent macrophages on PU, CH-Q and HA was distinct from those adherent to glass. Based on the 3-D shape factors, the degree of cell spreading was much lower on CH-Q and HA than on glass. HA and CH-Q are oppositely charged polymers, with the former being negative and the latter having a high positive charge. Despite this important difference the morphological responses of adherent macrophages on CH-Q and HA are remarkably similar, namely, similar values of cell surface areas, volumes, and $\varphi_{3D}$. These results lead us to believe that CH-Q and HA surfaces by themselves do not induce any dramatic changes in macrophage shape or size in response to surface contact. This is not the case for glass, which strongly stimulates adherent macrophages so that they enlarge and spread (FIG. 12A), resulting in large values for the surface area, volume, and 3-D shape factor.

The morphological responses of macrophages due to their interaction with biomaterial surfaces are also evident in the cell biofunctional/secretory response, as demonstrated by secretion levels of the pro-inflammatory cytokine TNF-α. Our assays of TNF-α levels for suspended plus adherent macrophages (FIG. 14A) indicate that glass stimulates the greatest amount of TNF-α production, whereas the CH-Q layer stimulates the least. For suspended plus adherent macrophages exposed to PU, TNF-α levels were similar to that of the HA surfaces. To investigate the bio-functional/secretory response of only the adherent macrophages, the suspended macrophages and PMA are removed, and then the adherent macrophages are cultured in fresh media for an additional three days without PMA (c.f., FIG. 9). Thus, TNF-α production after the additional three days of culturing can only be due to the adherent macrophages. On glass and PU, TNF-α secretion increased by a factor of ~2.5 compared to the level exhibited by the suspended plus adherent macrophages on glass and PU (with PMA) after the initial three day period. In contrast, macrophages on CH-Q and HA exhibited a decrease TNF-α secretion compared to the level produced by the suspended plus adherent cells on CH-Q and HA (with PMA) (FIGS. 14A and 14B). For the adherent macrophages on the four surfaces, the levels of TNF-α secretion are significantly different from each other (FIG. 14B). Our assays of TNF-α levels indicate that glass stimulates the greatest amount of TNF-α production, whereas the HA stimulates the least. This behavior, in part, results from the different cell density of macrophages on each surface. To account for this difference, TNF-α secretion level per adherent cell was determined for each surface. Normalized TNF-α secretion levels per adherent macrophage on each surface (FIG. 14C) clearly show that HA activates macrophages less and elicits a lower release of TNF-α than do the other surfaces. By rank order high to low, glass, PU, CH-Q, and HA surfaces provoke decreasing levels of TNF-α secretion.

In summary, these studies show both qualitatively and quantitatively that the morphological responses of adherent macrophages are related to their inflammatory cytokine-associated response. Namely, glass, PU, CH-Q, and HA surfaces provoke decreasing levels of TNF-α. Although similar on CH-Q and HA, the morphological response of adherent cells correlate with TNF-secretion; namely, cell spreading is largest on glass, less on PU and least on CH-Q and HA.

Conclusions

In this study, a GFP-actin expressing macrophage has enabled parallel studies of cell morphology and biofunctional response. To quantify biocompatibility, cell size, shape and associated cytokine secretion were measured. The data clearly demonstrate that the interaction between adherent macrophages and a biomaterial is significantly influenced by surface type. Specifically, the morphological appearance of adherent macrophages and their resultant cell functional activation states resulting in pro-inflammatory cytokine secretion are directly dependent on surface type. Namely, glass stimulated adherent macrophages to produce the highest level of TNF-α secretion, with successively lower amounts detected for PU, CH-Q, and HA surfaces. The morphological results of cell size, contact area and degree of spreading also generated a similar rank order, showing that both morphological and biofunctional measures can be used for biocompatibility evaluation.

Example 4: Tunable Swelling of Chitosan Brushes as a Function of Quaternary Ammonium Salt Substitution and Counterion Type As discussed in the previous examples, $CH-Q_{50}$ polymers, chitosans which were functionalized with quaternary ammonium salts (degree of substitution, DS=m=0.51), were grafted on GPTMS derivatized silicon oxide layers such as glass, silicon wafer, and silicon-oxide coated QCM crystal sensor. As shown above, these $CH-Q_{50}$ brushes exhibited symmetric pH-dependent swelling properties. Further studies were conducted to study the pH-dependent swelling as a function of quaternary ammonium salt substitution; to that end chitosan and $CH-Q_{25}$ polymers, chitosans which were functionalized with quaternary ammonium salts (DS=m=0.27) were prepared by a Michael reaction of chitosan (CH, Mw=60 kDa, degree of deacetylation=87%, l=0.13) with an acryl reagent (AETMAC). As determined by $^1$H-NMR for $CH-Q_{25}$, the monomer fractions of D-glucosamine (GlcN), N-alkylated D-glucosamine with quaternary ammonium salts (GlcN-Q), and N-acetyl-D-glucosamine (GlcNAc) are n=0.60, m=0.27, and l=0.13, respectively (Table 3).

Table 3 also shows that as the degree of substitution (DS: m=GlcN-Q monomer fraction) increases, the dry mass of grafted polymer and the contact angle decrease. As the degree of substitution, DS, increases, GlcN monomer fraction (n) decreases, resulting in a decrease of the number of primary amines for polymer grafting and decrease of the grafted density and dry thickness. As the DS increases, the number of quaternary ammonium cations of grafted polymer increase, and as a result, the brush surface becomes more hydrophilic.

The radius of gyration, $R_g$, of polymers in solutions during polymer grafting can also be a factor, affecting these results (table 1). As the number of quaternary ammonium cations (m) increases, the polymer grafted surface becomes more positively charged, resulting in increased electrostatic repulsion between polymer chains, polymer solubility improvement, and then % swelling increase of polymer brush. This suggests that the radius of gyration of chitosan can increase as the degree of substitution (DS=m) increases (i.e., the number of quaternary ammonium cations increases). FIG. 16 depicts that during the grafting process, $R_g$ of $CH-Q_{50}$ at the same pH solution (~45) is higher than that of CH (27.2~31.8 nm for Mw=60 kDa, $R_g$ (nm)=0.064$M_w^{0.55}$ or 0.075$M_w^{0.55}$). The large coil sizes of CH and $CH-Q_{50}$ polymers are attributed to chitosan's stiff wormlike chain characteristics as noted by a persistence length of 12~16 nm. In this process, the primary amines of a polymer chain react with the epoxide-derivatized $SiO_2$ surface inducing loops in polymer brush, unlike general polymer brush formation between end-group-functionalized polymer and specific grafting surfaces such as thiol-end-functionalized polystyrene and gold surfaces. During CH and CH-Q grafting processes, the values for layer height could be 2× the radii of gyration, $R_g$, of the corresponding chains floating freely in the pH solutions (FIG. 16). As a

TABLE 3

Mass deposited, grafting density, dry thickness, and contact angle for polymer brushes.

| Grafted polymer | Monomer fractions of polymer | | | Mass deposited (ng/cm$^2$)$^a$ | Grafting density (chains/nm$^2$)$^b$ | Thickness (nm)$^c$ | Contact angle (°, DI water) |
|---|---|---|---|---|---|---|---|
| | n | m | l | | | | |
| CH | 0.87 | 0 | 0.13 | 2847 | 0.29 | 52.7 | 20. ± 7 |
| $CH-Q_{25}$ | 0.60 | 0.27 | 0.13 | 1057 | 0.11 | 19.6 | 8. ± 3 |
| $CH-Q_{50}$ | 0.37 | 0.51 | 0.13 | 456 | 0.05 | 8.4 | ~0 |

$^{a,b,c}$Dry masses, grafting densities, and dry thicknesses were determined using the Sauerbrey equation, chitosan molecular weight, and density (cg10: Mw = 60 kDa, density = 0.54 g/cm$^3$).

To immobilize CH and $CH-Q_{25}$ on silicon oxide surfaces, the epoxide-amine reaction between GPTMS-derivatized $SiO_2$ surface and primary amine of D-glucosamine in chitosan polymer chains was used (FIG. 15). To maintain consistent reaction conditions, similar pH solutions (pH~4.5) of polymers were used for grafting the polymers on the GPTMS surface because of the different solubility for each polymer. For example, CH is insoluble in high pH (above ~6.5), while $CH-Q_{25}$ and $CH-Q_{50}$ are soluble over broad pH ranges (including high pH (~8)). To calculate the dry thicknesses of the polymer brushes for determination of the extent of swelling in aqueous media, the dry masses of the grafted polymers were determined using a QCM-D technique. The dry masses of CH, $CH-Q_{25}$, and $CH-Q_{50}$ brush layers have 2847, 1057, 456 ng/cm$^2$, and the water contact angles have 20, 8, and ~0, respectively (Table 3).

result, the dry thickness of the CH layer is higher than that of the $CH-Q_{50}$ layer because the CH polymer can be more grafted than CH-Q polymer with larger $R_g$ and higher water contents (FIG. 16 and Table 3).

In-situ swelling studies of CH, $CH-Q_{25}$, $CH-Q_{50}$ Brush Layers Using QCM-D In-Situ Swelling Studies of Chitosan Layer Depending on pH and Counteranion Type.

Chitosan behaves as a compact sphere in acetic acid with NaCl in solution or as a random coil in urea solution. The changes of charge density on chitosan resulting from pH changes and counteranion types can affect its conformation and then change its rheological properties. To study these properties, chitosan was grafted to epoxide derivatized silicon oxide and observed in-situ as a function of pH and different counteranion types using QCM-D. FIG. 17(a)

shows the QCM-D results for the immobilized chitosan layer on the $SiO_2$ coated sensor upon switching the pH of the solution. For the three modes (n=3, 5, 7), $\Delta f_n/n$ of the chitosan layer exposed to pH 8.02 solution are superimposed, and $\Delta D_n$ exhibits its lowest value, ~$7\times10^{-6}$, suggesting that the chitosan layer exhibits elastic behavior at pH 8.02 (the layer is an elastic and rigid film due to insolubleness of chitosan above the pH 6.5). Upon decreasing the pH from 8.02 to 3.63 ($Cl^-$ anion) (arrow 1), $\Delta f_n/n$ (n=3, 5, 7) decreases and the curves no longer superimpose, whereas $\Delta D_n$ increases. Thus an increase of protonated amine groups of the polymer chains within the layer at the reduced pH leads to increased electrostatic repulsion of cationic polymer chains and to increased water content of the layer and results in a swollen and viscous chitosan layer. Upon increasing the pH from 3.25 back to pH 8.02 (arrow 2), $\Delta f_n/n$ (n=3, 5, 7) and $\Delta D_n$ return to their original values, demonstrating that during the pH exposure the mass of chitosan grafted layer did not change and the chitosan layer is chemically stable. Furthermore, the increase and superposition of $\Delta f_n/n$ (n=3, 5, 7) and the decrease of $\Delta D_n$ show that the increase of neutral amine groups of polymer chains within the layer at the high pH leads the chitosan to become insoluable, resulting in expulsion of water from the swollen layer and return to the original elastic, rigid layer. Upon decreasing the pH from 8.02 to 7.06 (arrow 3), $\Delta f_n/n$ (n=3, 5, 7) and $\Delta D_n$ do not change. This means that the chitosan layer at pH 7.06 has similar properties (insolubility, elasticity) to the layer in pH 8.02. Upon decreasing the pH further from 7.06 to 5.46 (arrow 4), $\Delta f_n/n$ (n=3, 5, 7) and $\Delta D_n$ weakly decrease and increase, respectively. This result shows that the chitosan layer in pH 5.46 is more viscous and less elastic than the layer at pH 7.06 and 8.02. When the solution pH returns to 8.02, $\Delta f_n/n$ (n=3, 5, 7) and $\Delta D_n$ returns to original values. Collectively, these observations of CH layer show that as pH decreases below about pH 7 the layer become more viscous and swells, whereas in pH ranges (pH 7.06 and 8.02), the CH layer is elastic and rigid, and has similar properties.

To study counter anion effect on viscoelastic and swelling properties of CH brush layers, a pH 3.85 solution with acetate anions ($CH_3CO_2^-$) was prepared and exposed to the CH layer (arrow 6) and contrasted to the exposure of pH 3.63 solution with chloride anions ($Cl^-$) (arrow 1). Upon switching from pH 8.02 to pH 3.63 ($Cl^-$, arrow 1), $\Delta f_n/n$ (n=3, 5, 7) decrease to −415, −377, and −342, respectively and $\Delta D_n$ increase 53.4, 48.3, and 43.1, respectively. Upon switching from pH 8.02 to of pH 3.8 ($CH_3CO_2^-$, arrow 6), $\Delta f_n/n$ (n=3, 5, 7) decrease to −507, −440, and −390, respectively and $\Delta D_n$ increase 79.1, 75.1, and 71.0, respectively. Even though the exposed solutions have similar pH, the frequency decrease and dissipation increase of each mode on exposure of acetate anion solution (pH 3.8, $CH_3CO_2^-$, arrow 6) are bigger than that on exposure of chloride anion solution (pH 3.63, $Cl^-$, arrow 1), showing that the CH layer with acetate anions is more viscous and swollen than that with chloride anions. In similar acidic solutions at a given pH, CH brush layers have a similar protonated amine content of chitosan, but differ in the counter anions around the ammonium cation of chitosan polymer chains. The above data suggest that bigger counter anions ($CH_3CO_2^-$) induces the layer to be more viscous and swelling than smaller counter anions ($Cl^-$). After every subsequent change in pH (arrows 4, 5, 6, and 7) similar reversible behavior is observed when the solution pH returns to 8.02. These studies demonstrate that an immobilized CH layer is chemically stable over a wide pH range and exhibits reversible swelling and contraction that can be tuned by varying the pH and/or counter anions of the solution.

Physical properties of the layer such as thickness, shear modulus, and viscosity, can be calculated based on the fit using the Voigt based-viscoelastic model and the QCM-D experimental data. The CH-Q layer thicknesses obtained from the fit between the viscoelastic model and the experimental data ($\Delta f_n/n$ (n=3, 5, 7) and $\Delta D_n$), are plotted versus time (as a function of pH) in FIG. 17(b). At pH 8.20, the thickness of the chitosan layer is 53.1 nm (similar to dry thickness, 52.7 nm, in FIG. 15). Upon decreasing the pH from 8.20 to 3.63 (arrow 1), the layer thickness increases to 95 nm Upon increasing the pH from 3.63 back to pH 8.20 (arrow 2), the layer thickness returns to the original value of 53.1 nm. After each change in pH (arrows 4, 5, 6, and 7), the same thickness is recovered as expected for reversible behavior (arrow 1 and 2) when the solution pH returns to 8.02. Upon decreasing pH from 8.20 to 7.06 (arrow 3), the layer thickness does not change. When pH solutions were switched from 7.06 to 5.46, the layer thickness increases to 55. Upon increasing pH from 5.46 to 8.20, the layer thickness returns to the original value.

In order to study thickness changes depending on counter anion types, two different counter anions in similar pH solutions were exposed to the CH layer. While the layer thickness in pH 3.63 solution with chloride anion was 95 nm, the layer thickness in pH 3.85 solution with acetate anion shows a higher value of 120 nm.

Further studies of the in-situ swelling studies of the CH layer comparing acetate counter anions versus citrate anions are depicted in FIG. 20. Shown in FIG. 21 are the experimental results (a) comparing acetate and citrate anions and the fit of the experimental data with the viscoelastic model (b).

In-Situ Swelling Studies of $CH-Q_{25}$ Layer Depending on pH.

To better understand the pH-dependent swelling of chitosan brushes as a function of quaternary ammouium salt substitution, the $CH-Q_{25}$ polymer layer, grafted to the epoxide derivatized silicon oxide, was observed in-situ as a function of pH using QCM-D, compared to the pH-dependent swelling properties of CH and $CH-Q_{50}$ layers. FIG. 18(a) shows the QCM-D results for the immobilized $CH-Q_{25}$ layer on the $SiO_2$ coated sensor upon switching the pH of the solution. For the three modes (n=3, 5, 7), $\Delta f_n/n$ of the $CH-Q_{25}$ layer exposed to pH 5.46 (DI water) are superimposed, and $\Delta D_n$ exhibits its lowest value, ~$10\times10^{-6}$, suggesting that the $CH-Q_{25}$ layer exhibits elastic behavior at pH 5.46. Upon decreasing the pH from 5.46 to 3.63 ($Cl^-$ anion) (arrow 1), $\Delta f_n/n$ (n=3, 5, 7) decreases and the curves no longer superimpose, whereas $\Delta D_n$ increases. These changes mean that the reduced pH leads to increased water content of the layer, resulting in a swollen and viscous layer, similar in swelling to CH and $CH-Q_{50}$ layers at the reduced pH. Upon increasing the pH from 3.63 back to pH 5.46 (arrow 2), $\Delta f_n/n$ (n=3, 5, 7) and $\Delta D_n$ return to their original values. The increase and superposition of $\Delta f_n/n$ (n=3, 5, 7) and the decrease of $\Delta D_n$ mean that the high pH leads to expulsion of water from the CH-Q layer, resulting in the original elastic layer. Upon increasing the pH further from 5.46 to 7.06 (arrow 3), $\Delta f_n/n$ (n=3, 5, 7) and $\Delta D_n$ weakly increase and decrease, respectively. This result shows that the CH-Q layer in pH 7.06 is a little more elastic and less viscous than the layer in pH 5.46, similar to the CH polymer layer. By contrast, $CH-Q_{50}$ layer showed that increased pH (from 5 to 7) led to a frequency decrease and dissipation increase as a result of higher viscosity and lower elasticity. When the solution pH returns to 5.46 (arrow 4), $\Delta f_n/n$ (n=3, 5, 7) and $\Delta D_n$ return to the original values. Upon increasing the pH from 5.46 to 8.02 (arrow 5), $\Delta f_n/n$ (n=3, 5, 7) and $\Delta D_n$ weakly increase and decrease, respectively, similar to arrow 3. As pH decreases in the CH-$Q_{25}$ layer become more viscous and swelling, whereas in pH ranges (pH 7.06 and 8.02), the CH-$Q_{25}$ layer is more elastic and rigid, and has similar properties. When the CH-$Q_{25}$ layer was compared with CH and CH-$Q_{50}$ layers depending on pH change, the traces of frequency and dissipation changes of all three different layers are similar patterns at the reduced pH (to 3), in contrast, at increased pH (to 7, and 8), frequency and dissipation of CH-$Q_{25}$ has a similar trend to the CH layer, not to the CH-$Q_{50}$ layer which has higher degree of substitution of quaternary ammonium salts.

To study quaternary ammonium substitution effect on thicknesses of chitosan brush layers (as a function of pH change), the CH-$Q_{25}$ layer thicknesses obtained from the fit between the viscoelastic model and the experimental data ($\Delta f_n/n$ (n=3, 5, 7) and $\Delta D_n$), are plotted versus time (as a function of pH) in FIG. 18(b). Upon decreasing the pH from 5.46 to 3.63 (arrow 1), the layer thickness increases to 69 nm. Upon increasing pH from 3.63 back to pH 5.46 (arrow 2), the layer thickness returns to the original value of 43 nm. Upon decreasing pH from 5.46 to 7.06 and 8.20 (arrow 3 and 5), the layer thicknesses decreases to 40.6 nm and 40.4 nm, respectively. At pH 8.20 and 7.06, the thicknesses of the CH-$Q_{25}$ layer are not significantly different and show the smallest thickness which is ~2× higher than dry thickness of CH-$Q_{25}$ layer (19.6 nm, in Table 3). Similar to the CH layer, at pH 8.20 and 7.06, the thicknesses of the CH-$Q_{25}$ layer are not significantly different and show the lowest thickness (53.1 nm, FIG. 16(b)) which is the same for dry thickness of CH layer (52.7 in Table 3). This means that, in pH 8.20 and 7.06 solution, CH-$Q_{25}$ layer have infused water into original polymer layer and is swollen, CH layer has rarely infused water and is rigid thin layer.

Infused Water Fraction and Swelling Studies.

To study the pH dependent swelling behavior, the infused water content and percent swelling of CH, CH-$Q_{25}$, and CH-$Q_{50}$ layers at each pH and different counter anions were estimated from the volume and thickness of each dry polymer layer and each hydrated, swollen polymer layer determined from QCM-D. FIG. 19(a) shows, inter alia, the volume fractions of water in the CH layer at each pH and counter anion. At pH 7.06 and 8.20, the water fractions of CH layer exhibit minimum values of 0.01 and 0.01, respectively, meaning that at both pH solutions, the CH layer is 1% water and 99% CH, which is in agreement with chitosan's insolubility at high pH (above ~6.5). As the pH decreases from 8.20 to 5.46, the water fraction increase to 0.06. At pH 3.63 (with Cl⁻), the water volume fraction of the CH layer is 0.43. As the pH decreases, more water is infused into the CH layer. FIG. 19(a) also shows water content of the CH layer when two different counter anions in similar pH solutions were exposed to CH layer. While the water volume fraction of CH layer with chloride anion (pH 3.63) was 0.43, the water fraction of CH layer with acetate anion (pH 3.85) was 0.56. At similar pH, the infused water content in CH layer with acetate anions is 13% more than that with chloride anions.

For pH-dependent swelling studies as a function of quaternary ammonium cation substitution, the infused water content of CH-$Q_{25}$ layers in different pH solutions were also determined and compared with CH and CH-$Q_{50}$. In similar high acidic solutions (between pH 3 and 4, prepared with HCl), the water fractions of CH, CH-$Q_{25}$, and CH-$Q_{50}$ layers are 0.43, 0.72, and 0.83, respectively. As the degree of quaternary ammonium cation substitution of chitosan increase (DS=m=0, 0.27, and 0.51, FIG. 15 and Table 3), the water content of each polymer layers increase (43%, 72%, and 83%). This demonstrates that increasing the amount of chitosan substituted with quaternary ammonium cations induces more water infusion into the chains and higher electrostatic repulsion between positive charged polymer chains provides more room for water infusion. In week acidic solution (between pH 5 and 6), the water fractions of CH, CH-$Q_{25}$, and CH-$Q_{50}$ layers are 0.06, 0.54, 0.72, respectively. Even though the neutralized amine content of the polymer chains increase due to the pH increase, the CH-$Q_{25}$ and CH-$Q_{50}$ layers show 54% and 72% water content, respectively. By contrast, the CH layer without quaternary ammonium cations shows a dramatic decrease of infused water (6% water content). In acidic solutions, CH, CH-$Q_{25}$, and CH-$Q_{50}$ layers absorb more water as pH decreases (from week to high acidic solution).

In neutral and basic solutions (pH ~7 and ~8.5), the CH layer show little infused water (1% water in each pH), but the water fractions of the CH-$Q_{25}$ layer at both pH conditions have 51% water content. The water content of the CH-$Q_{50}$ layer are 80% and 90% at each pH, respectively.

FIG. 19(b) shows the percent swelling, determined for the dry thickness and the pH-dependent swollen thicknesses determined by QCM-D. At high acidic solutions (between pH 3 and 4, prepared with HCl), the percentage swellings of CH, CH-$Q_{25}$, and CH-$Q_{50}$ are 76%, 252%, and 476%, respectively. The layers are highly swollen with water at acidic solutions. As the degree of quaternary ammonium cation substitution of chitosan (DS=m) increases, the percent swelling of CH-$Q_{25}$ and CH-$Q_{50}$ (m=0.27 and 0.51, Table 3) show ~4× and ~6× the percent swelling of the CH layer (m=0), respectively. When the CH layer was exposed to similar pH solutions but different counter anion environments, the percent swellings of CH layer with chloride and with acetate anions are 76% and 128%, respectively. Percent swelling in CH layer with acetate anions shows ~2× that with chloride anions. In week acidic solution, percent swelling of CH, CH-$Q_{25}$, and CH-$Q_{50}$ layer are 6%, 107%, and 262%, respectively. In acidic solutions, CH, CH-$Q_{25}$, and CH-$Q_{50}$ layer exhibit increase of swelling behavior as pH decreases (from week to high acidic solution).

In neutral and basic solutions (pH ~7 and ~8.5), the CH layer in both solutions show the lowest percent swelling and same values (0.8% each), the percent swellings of CH-$Q_{25}$ in each pH solution are 107% and 106%, respectively. As pH value increases from 7.17 to 8.3, the percent swelling of CH-$Q_{50}$ layer increase from 398% to 908% (the highest percent swelling). The CH layer without quaternary ammonium cation does not exhibit swelling behavior in neutral and basic solution. By contrast CH-$Q_{25}$ layer with quaternary ammonium cations (DS=m=0.27) shows high and similar swelling behavior in both solutions, while the CH-$Q_{50}$ layer with quaternary ammonium cation (DS=m=0.51) shows highly increased swelling behavior as pH increases (from neutral to basic solution)

Finally, shown in FIG. 22 are (a) confocal fluorescence images of bacteria on $SiO_2$, CH, and CH-$Q_{50}$ surfaces depending on different shear stresses, and (b) normalized bacterial area coverage (%) depending on shear stresses for the various surfaces.

It will be appreciated by those skilled in the art that changes could be made to the embodiments described above without departing from the broad inventive concept thereof.

It is understood, therefore, that this invention is not limited to the particular embodiments disclosed, but it is intended to cover modifications that are within the spirit and scope of the invention, as defined by the appended claims.

What is claimed is:

1. An article comprising an implantable medical device and a composition covalently and stably immobilized to a surface of the device, wherein said composition comprises a chitosan modified with a quaternary ammonium salt, wherein at least about 25% of saccharide monomers of the chitosan are modified with the quaternary ammonium salt, wherein the immobilized composition has a pH ranging from pH3 to pH 9, and exhibits reversible, pH-dependent swelling and contraction of the composition.

2. The article of claim 1, wherein said composition further comprises an antimicrobial molecule.

3. The article of claim 1, wherein said composition further comprises an adhesion resistance molecule.

4. The article of claim 1, wherein said composition further comprises a molecule that prevents biocide leaching.

5. The article of claim 1, wherein said chitosan is operably linked to an antimicrobial molecule, an adhesion resistance molecule, a molecule that prevents biocide leaching, or a combination thereof.

6. The article of claim 1, wherein said surface is a silicon oxide surface.

7. The article of claim 1, wherein about 25% of saccharide monomers of said chitosan are modified with a quaternary ammonium salt.

8. The article of claim 1, wherein about 50% of saccharide monomers of said chitosan are modified with a quaternary ammonium salt.

9. The article of claim 1, wherein said quaternary ammonium salt comprises chloride anions.

10. The article of claim 1, wherein said quaternary ammonium salt is acetate anions.

11. The article of claim 1, wherein said quaternary ammonium salt comprises citrate anions.

12. The article of claim 1, wherein said article is a biomaterial.

13. The article of claim 1, wherein said article is a biomedical device.

14. The article of claim 13, wherein said biomedical device is a ventilator.

15. The article of claim 13, wherein said biomedical device is an endotracheal tube.

16. The article of claim 13, wherein said biomedical device is a device that comes in to contact with an environment in an animal.

17. The article of claim 13, wherein said surface on said device provides antimicrobial capability.

18. A composition comprising a chitosan modified with a quaternary ammonium salt, wherein at least about 25% of saccharide monomers of the chitosan are modified with the quaternary ammonium salt, wherein the composition has a pH ranging from pH 3 to pH 9, and exhibits reversible, pH-dependent swelling and contraction, and wherein said composition is capable of being immobilized on a surface to provide an antimicrobial activity.

19. The article of claim 1, wherein said composition is covalently immobilized to said surface via an amine group.

20. The article of claim 19, wherein said amine is a primary amine group.

* * * * *

UNITED STATES PATENT AND TRADEMARK OFFICE
CERTIFICATE OF CORRECTION

PATENT NO. : 9,950,097 B2
APPLICATION NO. : 13/983847
DATED : April 24, 2018
INVENTOR(S) : Hyun-Su Lee et al.

Page 1 of 1

It is certified that error appears in the above-identified patent and that said Letters Patent is hereby corrected as shown below:

In the Specification

Please replace Lines 17-21 in Column 1 with the following:
This invention was made with government support under grant number HL060230 awarded by the National Institutes of Health. The government has certain rights in the invention.

Signed and Sealed this
Twelfth Day of February, 2019

Andrei Iancu
*Director of the United States Patent and Trademark Office*